US009574196B2

(12) United States Patent
Giacalone et al.

(10) Patent No.: US 9,574,196 B2
(45) Date of Patent: *Feb. 21, 2017

(54) REGULATED GENETIC SUICIDE MECHANISM COMPOSITIONS AND METHODS

(71) Applicant: Vaxiion Therapeutics, LLC, San Diego, CA (US)

(72) Inventors: Matthew J Giacalone, San Diego, CA (US); Stanley Maloy, San Diego, CA (US); Shingo Tsuji, National City, CA (US)

(73) Assignee: Vaxiion Therapeutics, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/723,775

(22) Filed: May 28, 2015

(65) Prior Publication Data

US 2015/0344894 A1 Dec. 3, 2015

Related U.S. Application Data

(63) Continuation of application No. 13/711,482, filed on Dec. 11, 2012, now Pat. No. 9,045,761, which is a continuation of application No. 12/490,273, filed on Jun. 23, 2009, now abandoned.

(60) Provisional application No. 61/075,687, filed on Jun. 25, 2008, provisional application No. 61/168,457, filed on Apr. 10, 2009.

(51) Int. Cl.
*C12N 1/20* (2006.01)
*C12N 15/70* (2006.01)
*C12N 1/08* (2006.01)
*C12N 9/22* (2006.01)
*C12N 15/74* (2006.01)

(52) U.S. Cl.
CPC ............... *C12N 15/70* (2013.01); *C12N 1/08* (2013.01); *C12N 9/22* (2013.01); *C12N 15/74* (2013.01)

(58) Field of Classification Search
CPC ........... C12N 1/08; C12N 15/74; C12N 15/70; C12N 9/22
USPC ..................... 435/252.31, 252.3, 252.33, 252.34, 435/252.35
See application file for complete search history.

(56) References Cited

U.S. PATENT DOCUMENTS

| 4,895,724 | A | 1/1990 | Cardinal et al. |
|---|---|---|---|
| 5,314,695 | A | 5/1994 | Brown et al. |
| 9,045,761 | B2 * | 6/2015 | Giacalone ............... C12N 1/08 |
| 2003/0166279 | A1 | 9/2003 | Sabbadini et al. |
| 2003/0194798 | A1 | 10/2003 | Surber et al. |
| 2003/0207833 | A1 | 11/2003 | Berkley |
| 2004/0005700 | A1 | 1/2004 | Surber et al. |
| 2005/0147590 | A1 | 7/2005 | Sabbadini et al. |
| 2008/0038296 | A1 | 2/2008 | Brahmbhatt et al. |
| 2010/0112670 | A1 | 5/2010 | Giacalone et al. |

FOREIGN PATENT DOCUMENTS

| CN | 1 688 333 A | 10/2005 |
|---|---|---|
| WO | WO 03/033519 | 4/2003 |
| WO | WO 2004/113507 | 12/2004 |
| WO | WO 2005/056749 | 6/2005 |
| WO | WO 2005/079854 | 9/2005 |
| WO | WO 2006/021894 | 3/2006 |
| WO | WO 2006/055024 A2 | 5/2006 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Aagaard et al. "Intercellular mobility and homing of an archaeal rDNA intron confers a selective advantage over intron-cells of Sulfolobus acidocaldarius." Proc. Natl. Acad. Sci. USA, 1995, 92:12285-12289.
Burt et al. Homing endonuclease genes: the rise and fall and rise again of a selfish element, *Curr. Opin. Genet. Dev.*, 2004, 14(6):609-615.
Belfort et al. Mechanisms of Intron Mobility. J. Biol. Chem. 1995, 270(51):30237-30240.

(Continued)

*Primary Examiner* — Ganapathirama Raghu
(74) *Attorney, Agent, or Firm* — Knobbe Martens Olson & Bear LLP

(57) ABSTRACT

Embodiments of the present invention relates to the incorporation and use of a regulated genetic suicide mechanism for use in the improved purification of biologics, including adjunct use in various eubacterial minicell production and purification methodologies. Described herein are high-yield eubacterial minicell-producing strains with genetic modifications that comprise a regulated genetic suicide mechanism that irreparably destroys the parent cell chromosome such that live parental cells in a culture can be functionally eliminated at any time during the course of a minicell production and purification run. Embodiments of the present invention also describe methods useful in the elimination of live parental cells during the production of other cell-based biologics.

21 Claims, 9 Drawing Sheets

(56) References Cited

OTHER PUBLICATIONS

Chevalier et al. Flexible DNA Target Site Recognition by Divergent Homing Endonuclease Isoschizomers I-CreI and I-MsoI. *J. Mol. Biol.* 2003, 329:253-269.

Clementz et al. Function of the *Escherichia coli* msbB Gene, a Multicopy Suppressor of htrB Knockouts, in the Acylation of Lipid A, Journal of Biological chemistry, 272(16): 10353-10360 (1997).

Dodd et al. Construction of a physical and preliminary genetic map of Aeromonas hydrophila JMP636. *Microbiology* 1998, 144:3087-3096.

Erickson, "Evolution of the cytoskeleton", Bioessay 2007, 29(7):668-677.

Fernandez, Prokaryotic expression of antibodies and affibodies, *Current Opinion in Biotechnology* 2004, 15:364-373.

Giacalone et al. Immune responses elicited by bacterial minicells capable of simultaneous DNA and protein antigen delivery, *Vaccine* 2006, 24:pp. 6009-6017.

Giacalone et al. Immunization with non-replicating *E. coli* minicells delivering both protein antigen and DNA protects mice from lethal challenge with lymphocytic choriomeningitis virus. *Vaccine* 2007, 25:2279-2287.

Giacalone et al. The use of bacterial minicells to transfer plasmid DNA to eukaryotic cells. *Cellular Microbiology* 2006, 8(10):1624-1633.

Karow & Georgopoulos, Isolation and Characterization of the *Escherichia coli* msbB Gene, a Multicopy Suppressor of Null Mutations in the High-Temperature Requirement Gene htrB, Journal of Bacteriology, 174(3): 702-710 (1992).

Katayama et al. Rapid Expansion of the Physical and Genetic Map of the Chromosome of Clostridium perfringens CPN50. *Journal of Bacteriology*, 1995, 177(19):5680-5685.

Kjærgaard et al. Antigen 43-Mediated Autotransporter Display, a Versatile Bacterial Cell Surface Presentation System, *Journal of Bacteriology* 2002, 184(15):4197-4204.

Klauser et al. Characterization of the Neisseria Igaβ-core the essential unit for outer membrane targeting and extracellular protein secretion. *Journal of Molecular Biology* 1993, 234, pp. 579-593.

Kothapalli et al. Diversity of Genome Structure in *Salmonella enterica* Serovar Typhi Populations. *Journal of Bacteriology* 2005, 187(8):2638-2650.

Liu et al. Genomic mapping with I-CeuI, an intro-encoded endonuclease specific for genes for ribosomal RNA, in *Salmonella* spp., *Escherichia coli*, and other bacteria, *Proc. Natl. Acad. Sci. USA* 1993, 90:6874-6878.

Liu et al. Homologous recombination between rrn operons rearranges the chromosome in host-specialized species of *Salmonella*. *FEMS Microbiology Letters* 1998, 164:275-281.

Liu et al. I-CeuI Reveals Conservation of the Genome of Independent Strains of *Salmonella typhimurium*. *Journal of Bacteriology*, 1995, 177(11):3355-3357.

Macdiarmid et al. Bacterially Derived 400 nm Particles for Encapsulation and Cancer Cell Targeting of Chemotherapeutics, *Cancer Cell* 2007, 11:431-445.

Macdiarmid et al. Bacterially-derived nanocells for tumor-targeted delivery of chemotherapeutics and cell cycle inhibitors, *Cell Cycle* 2007, 6(17):1-7.

Marshall et al. The I-CeuI endonuclease : purification and potential role in the evolution of Chlamydomonas group I introns. *Eur. J. Biochem.* 1994, 220:855-859.

Marshall et al. The I-CeuI endonuclease recognizes a sequence of 19 base pairs and preferentially cleaves the coding strand of the Chlamydomonas moewusii chloroplast large subunit rRNA gene. *Nucleic Acids Research* 1992, 20(23):6401-6407.

Marshall, P. and C. Lemieux, Cleavage pattern of the homing endonuclease encoded by the fifth intron in the chloroplast large subunit rRNA-encoding gene of Chlamydomonas eugametos. *Gene* 1991, 104(2):241-245.

Qiu et al. Comparative Analysis of Physical Maps of Four Bacillus subtilis (natto) Genomes. *Applied and Environmental Microbiology* 2004, 70(10):6247-6256.

Ramos-Diaz et al. Combined Physical and Genetic Map of the Pseudomonas putida KT2440 Chromosome. *Journal of Bacteriology* 1998, 180(23):6352-6363.

Rutherford et al. Surface display of proteins by Gram-negative bacterial autotransporters, *Microbial Cell Factories* 2006, 5:22.

Schmidt et al. Comparative Genome Mapping of Pseudomonas aeruginosa PAO with P. aeruginosa C, Which Belongs to a Major Clone in Cystic Fibrosis Patients and Aquatic Habitats. *Journal of Bacteriology* 1996, 178(1):85-93.

Schulke et al., The homodimer of prostate-specific membrane antigen is a functional target for cancer therapy. PNAS, 2003, vol. 100 (22): 12590-12595.

Shu et al. I-CeuI fragment analysis of the *Shigella* species: evidence for large-scale chromosome rearrangement in *S. dysenteriae* and *S. flexneri*. *FEMS Microbiology Letters* 2000, 182:93-98.

Somerville et al., A Novel *Escherichia coli* Lipid A Mutant That Produces an Antiinflammatory Lipopolysaccharide, J. Clin. Invest., 97(2): 359-365 (1996).

Somerville et al., *Escherichia coli* msbB Gene as a Virulence Factor and a Therapeutic Target, Infection and Immunity, 67(12): 6583-6590 (1999).

Sozhamannan et al. Cloning and Sequencing of the Genes Downstream of the wbf Gene Cluster of Vibrio cholerae Serogroup O139 and Analysis of the Junction Genes in Other Serogroups. *Infection and Immunity* 1999, 67(10):5033-5040.

Spiegel et al. The Structure of I-CeuI Homing Endonuclease: Evolving Asymmetric DNA Recognition from a Symmetric Protein Scaffold. *Structure* 2006, 14:869-880.

Turmel et al. Evolutionarily conserved and functionally important residues in the I-CeuI homing endonuclease. *Nucleic Acids Research* 1997, 25(13):2610-2619.

Umelo et al. Physical map of the chromosome of Aeromonas salmonicida and genomic comparisons between Aeromonas strains. *Microbiology* 1998, 144:2141-2149.

Veiga et al. Neutralization of Enteric Coronaviruses with *Escherichia coli* Cells Expressing Single-Chain Fv-Autotransporter Fusions. *Journal of Virology* 2003, 77(24):13396-13398.

Veiga et al. Probing secretion and translocation of a β-autotransporter using a reporter single-chain Fv as a cognate passenger domain. *Molecular Microbiology* 1999, 33(6):1232-1243.

Veiga et al. Structural tolerance of bacterial autotransporters for folded passenger protein domains. *Molecular Microbiology* 2004, 52 (4):1069-1080.

Veiga et al. Autotransporters as scaffolds for novel bacterial adhesins: surface properties of *Escherichia coli* cells displaying Jun/Fos dimerization domains. *Journal of Bacteriology* 2003, 185(18):5585-5590.

International Search Report and Written Opinion dated Nov. 11, 2009 for PCT Patent Application PCT/US2009/048339, filed Jun. 23, 2009.

Restriction Requirement dated Aug. 30, 2011 for U.S. Appl. No. 12/490,273, filed Jun. 23, 2009.

Office Action dated Nov. 17, 2011 for U.S. Appl. No. 12/490,273, filed Jun. 23, 2009.

Final Office Action dated Jun. 11, 2012 for U.S. Appl. No. 12/490,273, filed Jun. 23, 2009.

Office Action dated Dec. 24, 2013 for Japanese Patent Application No. 2011-516548 filed Jun. 23, 2009.

Office Action dated May 3, 2012 for Chinese Patent Application No. 200980133155.X filed Jun. 23, 2009.

Office Action dated Mar. 8, 2013 for Chinese Patent Application No. 200980133155.X filed Jun. 23, 2009.

Office Action dated Nov. 14, 2013 for Chinese Patent Application No. 200980133155.X filed Jun. 23, 2009.

Office Action dated Nov. 14, 2013 for European Patent Application No. 09770897.8 filed Jun. 23, 2009.

Office Action dated Jun. 24, 2014 issued in Chinese Patent Application No. 200980133155.X filed Jun. 23, 2009.

Office Action dated Aug. 6, 2014 issued in European Patent Application No. 09770897.8 filed Jun. 23, 2009.

Office Action dated Sep. 5, 2014 issued in Australian Patent Application No. 2009262306, filed Jun. 23, 2009.

(56) References Cited

OTHER PUBLICATIONS

Office Action dated Oct. 28, 2014 issued in Japanese Patent Application No. 2011-516548, filed Jun. 23, 2009.
Low et al., "Lipid a mutant *Salmonella* with suppressed virulence and TNFalpha induction retain tumor-targeting In vivo". Nature Biotechnology vol. 17, 1999, pp. 37-41, XP055262485.
Low Kenneth Brooks et al., "Construction of VNP20009: a novel genetically stable antibiotic-sensitive strain of tumor-targeting *Salmonella* for parenteral administration in humans", Methods in Molecular Medicine, Humana Press, Totowa, NJ, vol. 90, 2004, pp. 47-60, XP008123456.
Ward et al., (1985) "Overproduction of FtsZ induces minicell formation in *E. coli*", Cell, vol. 42, No. 3, Oct. 1, pp. 941-949, XPO23911675.
Extended European Search Report dated Apr. 14, 2016 in European application No. 15194851.0.
Office Action dated Apr. 21, 2016 in Canadian Application No. 2729545.
Office Action dated May 17, 2016 issued in Japanese Application No. 2015-99338.

\* cited by examiner

- Glucose (0.2%) added at 0 hour
- Rhamnose (10 mM) added at 2.22 hours and OD of 0.3

FIGURE 4A
FIGURE 4B
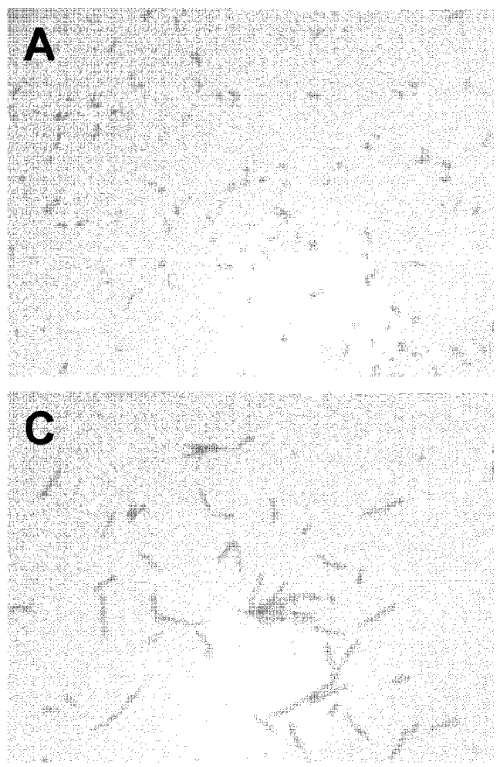
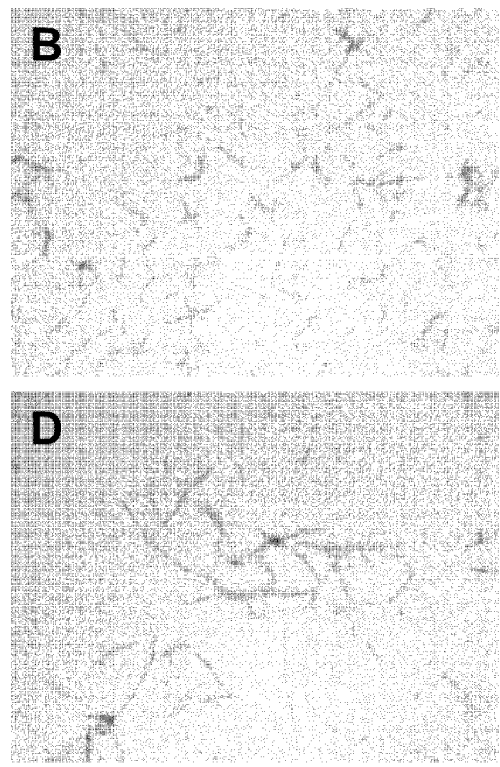
FIGURE 4C
FIGURE 4D

Single stranded I-CeuI DNA recognition sequence:

5' ...CGTAACTATAACGGTCCTAAGGTAGCGAA...3'   (SEQ ID NO: 2)

Double stranded I-CeuI DNA cleavage site:

5'...CGTAACTATAACGGTCCTAAGGTAGCGAA...3'   (SEQ ID NO: 7)
3'...GCATTGATATTGCCAGGATTCCATCGCTT...5'   (SEQ ID NO: 8)

FIGURE 9

```
                         SEQUENCE LISTING

<160> NUMBER OF SEQ ID NOS: 8

<210> SEQ ID NO 1
<211> LENGTH: 657
<212> TYPE: DNA
<213> ORGANISM: Chlamydomonas moewusii

<400> SEQUENCE: 1
atgtcaaact ttatacttaa accgggcgaa aaactacccc aagacaaact agaagaatta      60
aaaaaaatta atgatgctgt taaaaaaacg aaaaatttct caaaatactt gattgactta     120
agaaaacttt ttcaaattga cgaagtccaa gtaacttctg aatcaaaact cttttttagct    180 ggtttttttag aaggtgaagc ttctctaaat attagcacta aaaagctcgc tacttctaaa   240
tttggtttgg tggttgatcc tgaattcaat gtgactcaac atgtcaatgg ggttaaagtg     300
ctttatttag cattagaagt atttaaaaca gggcgtattc gtcataaaag tggtagtaat     360
gcaactttag ttttaactat tgacaatcgt caaagtttgg aagaaaaagt aattcctttc     420
tatgaacaat atgttgttgc cttcagttct ccagaaaaag tcaaacgtgt agctaattttt   480 aaagctttgt tagaattatt taataatgac gctcaccaag atttagaaca attggtaaac    540
aaaatcctac caatttggga tcaaatgcgt aaacaacaag gacaaagtaa cgaaggcttt    600
cctaatttag aagcagctca agactttgct cgtaattata aaaaaggtat aaagtag       657

<210> SEQ ID NO 2
<211> LENGTH: 29
<212> TYPE: DNA
<213> ORGANISM: Artificial Sequence
<220> FEATURE:
<223> OTHER INFORMATION: Single-Stranded I-CeuI DNA recognition site

<400> SEQUENCE: 2
cgtaactata acggtcctaa ggtagcgaa                                       29

<210> SEQ ID NO 3
<211> LENGTH: 383
<212> TYPE: PRT
<213> ORGANISM: Escherichia coli

<400> SEQUENCE: 3

Met Phe Glu Pro Met Glu Leu Thr Asn Asp Ala Val Ile Lys Val Ile
 1               5                  10                  15

Gly Val Gly Gly Gly Gly Gly Asn Ala Val Glu His Met Val Arg Glu
                20                  25                  30

Arg Ile Glu Gly Val Glu Phe Phe Ala Val Asn Thr Asp Ala Gln Ala
            35                  40                  45

Leu Arg Lys Thr Ala Val Gly Gln Thr Ile Gln Ile Gly Ser Gly Ile
        50                  55                  60

Thr Lys Gly Leu Gly Ala Gly Ala Asn Pro Glu Val Gly Arg Asn Ala
 65                  70                  75                  80

Ala Asp Glu Asp Arg Asp Ala Leu Arg Ala Ala Leu Glu Gly Ala Asp
                85                  90                  95

Met Val Phe Ile Ala Ala Gly Met Gly Gly Gly Thr Gly Thr Gly Ala
                100                 105                 110
```

```
Ala Pro Val Val Ala Glu Val Ala Lys Asp Leu Gly Ile Leu Thr Val
            115                 120                 125

Ala Val Val Thr Lys Pro Phe Asn Phe Glu Gly Lys Lys Arg Met Ala
        130                 135                 140

Phe Ala Glu Gln Gly Ile Thr Glu Leu Ser Lys His Val Asp Ser Leu
145                 150                 155                 160

Ile Thr Ile Pro Asn Asp Lys Leu Leu Lys Val Leu Gly Arg Gly Ile
                165                 170                 175

Ser Leu Leu Asp Ala Phe Gly Ala Ala Asn Asp Val Leu Lys Gly Ala
            180                 185                 190

Val Gln Gly Ile Ala Glu Leu Ile Thr Arg Pro Gly Leu Met Asn Val
        195                 200                 205

Asp Phe Ala Asp Val Arg Thr Val Met Ser Glu Met Gly Tyr Ala Met
    210                 215                 220

Met Gly Ser Gly Val Ala Ser Gly Glu Asp Arg Ala Glu Glu Ala Ala
225                 230                 235                 240

Glu Met Ala Ile Ser Ser Pro Leu Leu Glu Asp Ile Asp Leu Ser Gly
                245                 250                 255

Ala Arg Gly Val Leu Val Asn Ile Thr Ala Gly Phe Asp Leu Arg Leu
            260                 265                 270

Asp Glu Phe Glu Thr Val Gly Asn Thr Ile Arg Ala Phe Ala Ser Asp
        275                 280                 285

Asn Ala Thr Val Val Ile Gly Thr Ser Leu Asp Pro Asp Met Asn Asp
    290                 295                 300

Glu Leu Arg Val Thr Val Ala Thr Gly Ile Gly Met Asp Lys Arg
305                 310                 315                 320

Pro Glu Ile Thr Leu Val Thr Asn Lys Gln Val Gln Gln Pro Val Met
                325                 330                 335

Asp Arg Tyr Gln Gln His Gly Met Ala Pro Leu Thr Gln Glu Gln Lys
            340                 345                 350

Pro Val Ala Lys Val Val Asn Asp Asn Ala Pro Gln Thr Ala Lys Glu
        355                 360                 365

Pro Asp Tyr Leu Asp Ile Pro Ala Phe Leu Arg Lys Gln Ala Asp
    370                 375                 380

<210> SEQ ID NO 4
<211> LENGTH: 218
<212> TYPE: PRT
<213> ORGANISM: Chlamydomonas moewusii

<400> SEQUENCE: 4

Met Ser Asn Phe Ile Leu Lys Pro Gly Glu Lys Leu Pro Gln Asp Lys
1               5                   10                  15

Leu Glu Glu Leu Lys Lys Ile Asn Asp Ala Val Lys Lys Thr Lys Asn
            20                  25                  30

Phe Ser Lys Tyr Leu Ile Asp Leu Arg Lys Leu Phe Gln Ile Asp Glu
        35                  40                  45

Val Gln Val Thr Ser Glu Ser Lys Leu Phe Leu Ala Gly Phe Leu Glu
    50                  55                  60

Gly Glu Ala Ser Leu Asn Ile Ser Thr Lys Lys Leu Ala Thr Ser Lys
65                  70                  75                  80

Phe Gly Leu Val Val Asp Pro Glu Phe Asn Val Thr Gln His Val Asn
                85                  90                  95

Gly Val Lys Val Leu Tyr Leu Ala Leu Glu Val Phe Lys Thr Gly Arg
            100                 105                 110
```

```
Ile Arg His Lys Ser Gly Ser Asn Ala Thr Leu Val Leu Thr Ile Asp
        115                 120                 125

Asn Arg Gln Ser Leu Glu Glu Lys Val Ile Pro Phe Tyr Glu Gln Tyr
    130                 135                 140

Val Val Ala Phe Ser Ser Pro Glu Lys Val Lys Arg Val Ala Asn Phe
145                 150                 155                 160

Lys Ala Leu Leu Glu Leu Phe Asn Asn Asp Ala His Gln Asp Leu Glu
                165                 170                 175

Gln Leu Val Asn Lys Ile Leu Pro Ile Trp Asp Gln Met Arg Lys Gln
            180                 185                 190

Gln Gly Gln Ser Asn Glu Gly Phe Pro Asn Leu Glu Ala Ala Gln Asp
        195                 200                 205

Phe Ala Arg Asn Tyr Lys Lys Gly Ile Lys
        210                 215

<210> SEQ ID NO 5
<211> LENGTH: 9446
<212> TYPE: DNA
<213> ORGANISM: Artificial Sequence
<220> FEATURE:
<223> OTHER INFORMATION: pVX-66 integration vector (RK6 origin of
      replication; I-CeuI under cI857ts promoter
      control; FtsZ under IPTG inducible promoter
      control; proBA; attpP)

<400> SEQUENCE: 5
tctagaaacc atggaagcta gcgaacttac tttataccct ttttataatt acgagcaaag     60
tcttgagctg cttctaaatt aggaaagcct tcgttacttt gtccttgttg tttacgcatt    120
tgatcccaaa ttggtaggat tttgtttacc aattgttcta atcttggtg agcgtcatta     180 ttaaataatt ctaacaaagc tttaaaatta gctacacgtt tgacttttc tggagaactg    240 aaggcaacaa catattgttc ataaaaagga attacttttt cttccaaact ttgacgattg    300
tcaatagtta aaactaaagt tgcattacta ccacttttat gacgaatacg ccctgtttta    360
aatacttcta atgctaaata aagcacttta accccattga catgttgagt cacattgaat    420
tcaggatcaa ccaccaaacc aaatttagaa gtagcgagct tttagtgct aatatttaga    480 gaagcttcac cttctaaaaa accagctaaa aagagttttg attcagaagt tacttggact    540
tcgtcaattt gaaaaagttt tcttaagtca atcaagtatt tgagaaaatt tttcgttttt    600
ttaacagcat cattaatttt tttaattct tctagtttgt cttggggtag tttttcgccc     660
ggtttaagta taaagtttga catgagttat ttcctcctaa aactcgaggc gccaatgctt    720
cgtttcgtat cacacacccc aaagccttct gctttgaatg ctgcccttct tcagggctta    780
atttttaaga gcgtcacctt catggtggtc agtgcgtcct gctgatgtgc tcagtatcac    840
cgccagtggt atttatgtca acaccgccag agataattta tcaccgcaga tggttatctg    900
tatgtttttt atatgaattt attttttgca gggggcatt gtttggtagg tgagagatcc     960 ccgggggca gaactcaaaa attccggtgc aaaacagaca ggcgaaacac tgaagatcaa   1020
cattcttgat ctttagctgt cttggtttgc ccaaagcgca ttgcataatc tttcaggtt    1080 atgcgttgtt ccatacaacc tcctagtac atgcaaccat tatcaccgcc agaggtaaaa    1140
tagtcaacac gcacggtgtt agatatttat cccttgcggt gatagattta acgtatgagc    1200
acaaaaaaga aaccattaac acaagagcag cttgaggacg cacgtcgcct taaagcaatt    1260
tatgaaaaaa agaaaaatga acttggctta tcccaggaat ctgtcgcaga caagatgggg    1320
```

```
atgggcagt caggcgttgg tgctttattt aatggcatca atgcattaaa tgcttataac    1380
gccgcattgc ttgcaaaaat tctcaaagtt agcgttgaag aatttagccc ttcaatcgcc    1440
agagaaatct acgagatgta tgaagcggtt agtatgcagc cgtcacttag aagtgagtat    1500
gagtaccctg ttttttctca tgttcaggca gggatgttct cacctaagct tagaaccttt    1560
accaaaggtg atgcggagag atgggtaagc acaaccaaaa aagccagtga ttctgcattc    1620
tggcttgagg ttgaaggtaa ttccatgacc gcaccaacag gctccaagcc aagctttcct    1680
gacggaatgt taattctcgt tgaccctgag caggctgttg agccaggtga tttctgcata    1740
gccagacttg ggggtgatga gtttaccttc aagaaactga tcagggatag cggtcaggtg    1800
ttttttacaac cactaaaccc acagtaccca atgatcccat gcaatgagag ttgttccgtt    1860
gtggggaaag ttatcgctag tcagtggcct gaagagacgt ttggctgatc ccacagccgc    1920
cagttccgct ggcggcattt tggatccact agtaacggcc gccagtgtgc tggaattcgc    1980
ccttcaaggt taaaactaag gtaccatgcg tcaatggcct tgtgaatcaa atggctactt    2040
ttgcatcacc cggtttattt tacgcacgaa tggtgtaatc accaatgccg atccacttgt    2100
aagtggtcag tgcttccagc ccattgggc cacgcgcgtg agttttttgt gtgcttaccg    2160
ccacttccgc acccagacca aactggccgc cgtcggtaaa acgcgtagag cgttaacgt    2220
aaacagcgga cgaatccact tcgttaacaa aacgctgggc gttgcgcata tcgcgggtca    2280
ggatcgcatc ggagtgttgt gtgccgtgtt cacgaatatg ggcgatggca tcgtcaagat    2340
cgctgacgat tttgacgttc aaatctaatg acagaaactc atcgtcatac tcttcggctt    2400
taacagcaac caccttcgca gggcctgcct gcaactgcgc cagtgcagct gcatctgcgt    2460
gtaatgtcac gccgctttcc gccatttgtt tgcttaatgc gggcaggaag ctatcggcga    2520
tgtttttatt caccagcaac gtttcaaccg tattacatgt gctcggacgc tgagttttcg    2580
cgttgacgat cacttttaat gcttcagcga tctctacact ttcatcaacg taaatatggc    2640
atacgcctat accacctgtg atcaccggga ttgtcgactg ttcacggcac agtttatgca    2700
aaccagcgcc accacgcggg atcagcatgt cgatgtattt atccatacgc agcatttcac    2760
tgaccagcgc acggtcagga ttatcaatcg cctgcacggc acccgccggt aagccgcagg    2820
atttcagggc gtcctgaatc accgccaccg ttgcagcgtt agtgcgacac gtttctttgc    2880
caccgcgcag gatcaccgca ttaccggttt tcaggcacag cgaagcgaca tcaaccgtca    2940
cgttcgggcg cgcttcataa atcacgccaa taaccccag cggtacgcga cgacgctcaa    3000
gacgcaggcc gctgtccagt acgccgccat cgattacctg ccccaccgga tcggcgaggt    3060
tgcacacctg acgtacatcg tcggcaatgc ctttcagccg tgcgggcgtc agtgccagac    3120
ggtcaagcat cgcttcgcta aggccattgg ctcgcgcgtc agcaacatcc tgggcgttag    3180
cgttgaggat gatttcgctt tgtgcttcca gttcatcggc gattttttcc agcacgcgat    3240
tttttttcgcg gctggagagt tgcgctaatt tatacgaggc ttgcttcgcg gcaatgccca    3300
tttgttccag catcagcctg ctccttaacg ggtaatcatg tcatcacggt gaacggcaac    3360
cgggccgtat tcatatccca gtattgcatc aatttcttgc gagtggtgtc cggcaatacg    3420
gcgtaatgca tcgctgttgt aacgactgac gccgtgggcg atatcgcggc cttcgaggtt    3480
gcaaatgcgg atgacttcac cacgcgagaa attgccagtc acgcttttaa tgcctttcgg    3540
caacagggag ctgccgcgtt ccagaatggc ggcagttgcc ccttcatcta ccgtgatttc    3600
acccgccggc ggcgcaccga aaatccgcg tttacggttt tcaagcggag tcgcctgggc    3660
atggaacagc gtaccgacgg aaatgccttc catcacatca ccaataacgc ccggcttgct    3720
```

```
gcccgcggca ataatggtgt cgatacccgc acggcaagcc acgtcagcgg cctgcaattt      3780
ggtactcatg ccgccagttc cgaggcctga aacgctgtca ccggcaatcg cgcgcagtgc      3840
gtcatcaatg ccgtaaacat ctttaatcag ttctgcctgc ggattgctgc gcgggtcagc      3900
ggtatacaaa ccttttttgat cggtcagcag caacagttta tcggcacccg caagaatcgc      3960
cgccagcgca gaaaggttat cgttatcgcc gaccttaatc tctgccgtag cgacagcatc      4020
gttctcattg attaccggaa cgatattgtt atcgagcaac gctcgcaggg tgtcgcgggc      4080
gttcaggaag cgttcacggt cttccatatc agcacgggtc agcagcattt gcccgacgtg      4140
aatgccataa atcgaaaaca gctgttccca cagttgaatc agtcgactct gccctaccgc      4200
cgccagcagt tgtttcgagg cgatggtcgc tggcagttcc gggtaaccca ggtgctcacg      4260
tccggcggcg atcgcgcccg acgtcacaat aacaatccga tgcccggcgg catgtaactg      4320
cgcgcactgg cgaacaagtt caacgatatg ggcacggttc agacggcgcg atccgcctgt      4380
tagcacactg gtgccgagtt ttaccaccag cgtctggctg tcactcatga ttctctgcca      4440
ttcaatttta ggaaaaatga tatcaaacga acgttttagc aggactgtcg tcggttgcca      4500
accatctgcg agcaaagcat ggcgttttgt tgcgcgatct gtaataaaag cgtaaacgca      4560
tgcgatatcg agctctcccg ggaattcttg cgctaatgct ctgttacagg tcactaatac      4620
catctaagta gttgattcat agtgactgca tatgttgtgt tttacagtat tatgtagtct      4680
gttttttatg caaaatctaa tttaatatat tgatatttat atcattttac gtttctcgtt      4740 cagcttttttt atactaagtt ggcattataa aaaagcattg cttatcaatt tgttgcaacg      4800
aacaggtcac tatcagtcaa aataaaatca ttatttgatt tcaattttgt cccgaattcg      4860
atcgctagtt tgttttgact ccatccatta gggcttctaa aacgccttct aaggccatgt      4920
cagccgttaa gtgttcctgt gtcactgaaa attgctttga gaggctctaa gggcttctca      4980
gtgcgttaca tccctggctt gttgtccaca accgttaaac cttaaaagct ttaaaagcct      5040
tatatattct tttttttctt ataaaactta aaaccttaga ggctatttaa gttgctgatt      5100
tatattaatt ttattgttca aacatgagag cttagtacgt gaaacatgag agcttagtac      5160
gttagccatg agagcttagt acgttagcca tgagggttta gttcgttaaa catgagagct      5220
tagtacgtta acatgagag cttagtacgt gaaacatgag agcttagtac gtactatcaa      5280
caggttgaac tgcggatctt gcggccgcat tcccaattcc aggcatcaaa taaaacgaaa      5340
ggctcagtcg aaagactggg cctttcgttt tatctgttgt tgtcggtga acgctctcct      5400 gagtaggaca aatccgccgg agcggattt gaacgttgcg aagcaacggc ccggagggtg      5460
gcgggcagga cgcccgccat aaactgccag gaattaattc caggcatcaa ataaaacgaa      5520
aggctcagtc gaaagactgg gcctttcgtt ttatctgttg tttgtcggtg aacgctctcc      5580
tgagtaggac aaatccgccg ggagcggatt tgaacgttgc gaagcaacgg cccggagggt      5640
ggcgggcagg acgcccgcca taaactgcca ggaattaatt ccaggcatca ataaaacgaa      5700
aggctcagtc gaaagactgg gcctttcgtt ttatctgttg tttgtcggtg aacgctctct      5760
ctgagtagga caaatccgcc gggagcggat ttgaacgttg cgaagcaacg cccggaggg      5820 tggcgggcag gacgcccgcc ataaactgcc aggaattaat ccaggcatc aaataaaacg      5880 aaaggctcag tcgaaagact gggcctttcg tttatctgt gtttgtcgg tgaacgctct      5940 cctgagtagg acaaatccgc cgggagcgga tttgaacgtt gcgaagcaac ggcccggagg      6000
gtggcgggca ggacgcccgc cataaactgc caggaattgg ggatcggaat tcgacgaacg      6060
```

```
ccagcaagac gtagcccagc gcgtcggcca gcttgcaatt cgcgctaact tacattaatt      6120
gcgttgcgct cactgcccgc tttccagtcg ggaaacctgt cgtgccagct gcattaatga      6180
atcggccaac gcgcggggag aggcggtttg cgtattgggc gccagggtgg ttttcttttt      6240
caccagtgag acgggcaaca gctgattgcc cttcaccgcc tggccctgag agagttgcag      6300
caagcggtcc acgctggttt gccccagcag gcgaaaatcc tgtttgatgg tggttgacgg      6360
cgggatataa catgagctgt cttcggtatc gtcgtatccc actaccgaga tatccgcacc      6420
aacgcgcagc ccggactcgg taatggcgcg cattgcgccc agcgccatct gatcgttggc      6480
aaccagcatc gcagtgggaa cgatgccctc attcagcatt tgcatggttt gttgaaaacc      6540
ggacatggca ctccagtcgc cttcccgttc cgctatcggc tgaatttgat tgcgagtgag      6600
atatttatgc cagccagcca gacgcagacg cgccgagaca gaacttaatg ggcccgctaa      6660
cagcgcgatt tgctggtgac ccaatgcgac cagatgctcc acgcccagtc gcgtaccgtc      6720
ttcatgggag aaaataatac tgttgatggg tgtctggtca gagacatcaa gaaataacgc      6780
cggaacatta gtgcaggcag cttccacagc aatggcatcc tggtcatcca gcggatagtt      6840
aatgatcagc ccactgacgc gttgcgcgag aagattgtgc accgccgctt tacaggcttc      6900
gacgccgctt cgttctacca tcgacaccac cacgctggca cccagttgat cggcgcgaga      6960
tttaatcgcc gcgacaattt gcgacggcgc gtgcagggcc agactggagg tggcaacgcc      7020
aatcagcaac gactgtttgc cgccagttg ttgtgccacg cggttgggaa tgtaattcag      7080
ctccgccatc gccgcttcca cttttttccg cgttttcgca gaaacgtggc tggcctggtt      7140
caccacgcgg gaaacggtct gataagagac accggcatac tctgcgacat cgtataacgt      7200
tactggtttc acattcacca ccctgaattg actctcttcc gggcgctatc atgccatacc      7260
gcgaaaggtt ttgcaccatt cgatggtgtc aacgtaaatg ccgcttcgcc ttcgcgcgcg      7320
aattgcaagc tgatccgggc ttatcgactg cacggtgcac caatgcttct ggcgtcaggc      7380
agccatcgga agctgtggta tggctgtgca ggtcgtaaat cactgcataa ttcgtgtcgc      7440
tcaaggcgca ctcccgttct ggataatgtt ttttgcgccg acatcataac ggttctggca      7500
aatattctga aatgagctgt tgacaattaa tcatcggctc gtataacgtg tggaattgtg      7560
agcggataat aatttcacac aggaaacaga attaattccc ggggatctca ggcgacaggc      7620
acaaatcgga gagaaactat gtttgaacca atggaactta ccaatgacgc ggtgattaaa      7680
gtcatcggcg tcggcggcgg cggcggtaat gctgttgaac acatggtgcg cgagcgcatt      7740
gaaggtgttg aattcttcgc ggtaaatacc gatgcacaag cgctgcgtaa acagcggtt       7800 ggacagacga ttcaaatcgg tagcggtatc accaaaggac tgggcgctgg cgctaatcca      7860
gaagttggcc gcaatgcggc tgatgaggat cgcgatgcat tgcgtgcggc gctggaaggt      7920
gcagacatgg tctttattgc tgcgggtatg ggtggtggta ccggtacagg tgcagcacca      7980
gtcgtcgctg aagtggcaaa agatttgggt atcctgaccg ttgctgtcgt cactaagcct      8040
ttcaactttg aaggcaagaa gcgtatggca ttcgcggagc aggggatcac tgaactgtcc      8100
aagcatgtgg actctctgat cactatcccg aacgacaaac tgctgaaagt tctgggccgc      8160
ggtatctccc tgctggatgc gtttggcgca gcgaacgatg tactgaaagg cgctgtgcaa      8220
ggtatcgctg aactgattac tcgtccgggt ttgatgaacg tggactttgc agacgtacgc      8280
accgtaatgt ctgagatggg ctacgcaatg atgggttctg gcgtggcgag cggtgaagac      8340
cgtgcggaag aagctgctga aatggctatc tcttctccgc tgctggaaga tatcgacctg      8400
tctggcgcgc gcggcgtgct ggttaacatc acggcgggct tcgacctgcg tctggatgag      8460
```

-continued

```
ttcgaaacgg taggtaacac catccgtgca tttgcttccg acaacgcgac tgtggttatc    8520
ggtacttctc ttgaccccgga tatgaatgac gagctgcgcg taaccgttgt tgcgacaggt    8580
atcggcatgg acaaacgtcc tgaaatcact ctggtgacca ataagcaggt tcagcagcca    8640
gtgatggatc gctaccagca gcatgggatg gctccgctga cccaggagca gaagccggtt    8700
gctaaagtcg tgaatgacaa tgcgccgcaa actgcgaaag agccggatta tctggatatc    8760
ccagcattcc tgcgtaagca agctgattaa gaattgactg gaatttgggt ttcgaggctc    8820
tttgtgctaa actggcccgc cgaatgtata gtacacttcg gttggatagg taatttggcg    8880
agataatacg atgatcaaac aaaggacact taaacgtatc gttcaggcga cgggtgtcgg    8940
tttacatacc ggcaagaaag tcaccctgac gttacgccct gcgccggcca acaccggggt    9000
catctatcgt cgcaccgact tgaatccacc ggtagatttc ccggccgatg ccaaatctgt    9060
gcgtgatacc atgctctgta cgtgtctggt caacgagcat gatgtacgga tttcaaccgt    9120
agagcacctc aatgctgctc tcgcgggctt gggcatcgat ggcccccga tggtagtgtg    9180 gggtctcccc atgcgagagt agggaactgc caggcatcaa ataaaacgaa aggctcagtc    9240
gaaagactgg gcctttcgtt ttatctgttg tttgtcggtg aacgctctcc tgagtaggac    9300
aaatccgccg ggagcggatt tgaacgttgc gaagcaacgg cccggagggt ggcgggcagg    9360
acgcccgcca taaactgcca ggcatcaaat taagcagaag gccatcctga cggatggcct    9420
ttttgcgtgg ccagtgccaa gcttct                                         9446
```

<210> SEQ ID NO 6
<211> LENGTH: 6251
<212> TYPE: DNA
<213> ORGANISM: Artificial Sequence
<220> FEATURE:
<223> OTHER INFORMATION: pVX-55 expression vector (contains I-CeuI gene
      under the control of the rhamnose inducible pRHA
      promoter system)

<400> SEQUENCE: 6

```
aagggcgaat tctgcagata tccatcacac tggcggccgc tcgagcatgc atctagaggg      60
cccaattcgc cctatagtga gtcgtattac aattcactgg ccgtcgtttt acaacgtcgt     120
gactgggaaa accctggcgt tacccaactt aatcgccttg cagcacatcc cccttcgcc     180 agctggcgta atagcgaaga ggcccgcacc gatcgccctt cccaacagtt gcgcagccta     240
tacgtacggc agtttaaggt ttacacctat aaaagagaga gccgttatcg tctgtttgtg     300
gatgtacaga gtgatattat tgacacgccg gggcgacgga tggtgatccc cctggccagt     360
gcacgtctgc tgtcagataa agtctcccgt gaactttacc cggtggtgca tatcggggat     420
gaaagctggc gcatgatgac caccgatatg gccagtgtgc cggtctccgt tatcggggaa     480
gaagtggctg atctcagcca ccgcgaaaat gacatcaaaa acgccattaa cctgatgttc     540 tgggaatat aaatgtcagg catgagatta tcaaaaagga tcttcaccta gatccttttc     600
acgtagaaag ccagtccgca gaaacggtgc tgaccccgga tgaatgtcag ctactgggct     660
atctggacaa gggaaaacgc aagcgcaaag agaaagcagg tagcttgcag tgggcttaca     720
tggcgatagc tagactgggc ggttttatgg acagcaagcg aaccggaatt gccagctggg     780
gcgccctctg gtaaggttgg gaagccctgc aaagtaaact ggatggcttt ctcgccgcca     840
aggatctgat ggcgcagggg atcaagctct gatcaagaga caggatgagg atcgtttcgc     900
atgattgaac aagatggatt gcacgcaggt tctccggccg cttgggtgga gaggctattc     960
```

```
ggctatgact gggcacaaca gacaatcggc tgctctgatg ccgccgtgtt ccggctgtca    1020
gcgcaggggc gcccggttct ttttgtcaag accgacctgt ccggtgccct gaatgaactg    1080
caagacgagg cagcgcggct atcgtggctg ccacgacgg gcgttccttg cgcagctgtg    1140
ctcgacgttg tcactgaagc gggaagggac tggctgctat tgggcgaagt gccggggcag    1200
gatctcctgt catctcacct tgctcctgcc gagaaagtat ccatcatggc tgatgcaatg    1260
cggcggctgc atacgcttga tccggctacc tgcccattcg accaccaagc gaaacatcgc    1320
atcgagcgag cacgtactcg gatggaagcc ggtcttgtcg atcaggatga tctggacgaa    1380
gagcatcagg ggctcgcgcc agccgaactg ttcgccaggc tcaaggcgag catgcccgac    1440
ggcgaggatc tcgtcgtgac ccatggcgat gcctgcttgc cgaatatcat ggtggaaaat    1500
ggccgctttt ctggattcat cgactgtggc cggctgggtg tggcggaccg ctatcaggac    1560
atagcgttgg ctacccgtga tattgctgaa gagcttggcg gcgaatgggc tgaccgcttc    1620
ctcgtgcttt acggtatcgc cgctcccgat tcgcagcgca tcgccttcta tcgccttctt    1680
gacgagttct tctgaattat taacgcttac aatttcctga tgcggtattt tctccttacg    1740
catctgtgcg gtatttcaca ccgcatacag gtggcacttt tcggggaaat gtgcgcggaa    1800
cccctatttg tttatttttc taaatacatt caaatatgta tccgctcatg agacaataac    1860
cctgataaat gcttcaataa tagcacgtga gagggccac catggccaag ttgaccagtg    1920
ccgttccggt gctcaccgcg cgcgacgtcg ccggagcggt cgagttctgg accgaccggc    1980
tcgggttctc ccgggacttc gtggaggacg acttcgccgg tgtggtccgg gacgacgtga    2040
ccctgttcat cagcgcggtc caggaccagg tggtgccgga caacaccctg gcctgggtgt    2100
gggtgcgcgg cctggacgag ctgtacgccg agtggtcgga ggtcgtgtcc acgaacttcc    2160
gggacgcctc cggccggcc atgaccgaga tcggcgagca gccgtggggg cgggagttcg    2220
ccctgcgcga cccggccggc aactgcgtgc acttcgtggc cgaggagcag gactgacacg    2280
tgctaaaact tcatttttaa tttaaaagga tctaggtgaa gatcctttt gataatctca    2340 tgaccaaaat cccttaacgt gagttttcgt tccactgagc gtcagacccc gtagaaaaga    2400
tcaaaggatc ttcttgagat cctttttttc tgcgcgtaat ctgctgcttg caaacaaaaa    2460
aaccaccgct accagcggtg gtttgtttgc cggatcaaga gctaccaact ctttttccga    2520
aggtaactgg cttcagcaga gcgcagatac caaatactgt ccttctagtg tagccgtagt    2580
taggccacca cttcaagaac tctgtagcac cgcctacata cctcgctctg ctaatcctgt    2640
taccagtggc tgctgccagt ggcgataagt cgtgtcttac cgggttggac tcaagacgat    2700
agttaccgga taaggcgcag cggtcgggct gaacggggg ttcgtgcaca cagcccagct    2760
tggagcgaac gacctacacc gaactgagat acctacagcg tgagctatga aaagcgcca    2820 cgcttcccga agggagaaag gcggacaggt atccggtaag cggcagggtc ggaacaggag    2880
agcgcacgag ggagcttcca gggggaaacg cctggtatct ttatagtcct gtcgggtttc    2940
gccacctctg acttgagcgt cgatttttgt gatgctcgtc agggggggcgg agcctatgga    3000 aaaacgccag caacgcggcc tttttacggt tcctgggctt ttgctggcct tttgctcaca    3060
tgttctttcc tgcgttatcc cctgattctg tggataaccg tattaccgcc tttgagtgag    3120
ctgataccgc tcgccgcagc cgaacgaccg agcgcagcga gtcagtgagc gaggaagcgg    3180
aagagcgccc aatacgcaaa ccgcctctcc ccgcgcgttg gccgattcat taatgcagct    3240
ggcacgacag gtttcccgac tggaaagcgg gcagtgagcg caacgcaatt aatgtgagtt    3300
agctcactca ttaggcaccc caggctttac actttatgct tccggctcgt atgttgtgtg    3360
```

```
gaattgtgag cggataacaa tttcacacag gaaacagcta tgaccatgat tacgccaagc  3420
tatttaggtg acactataga atactcaagc tatgcatcaa gcttggtacc gagctcggat  3480
ccactagtaa cggccgccag tgtgctggaa ttcgccgttt ctagaattaa tctttctgcg  3540
aattgagatg acgccactgg ctgggcgtca tcccggtttc ccgggtaaac accaccgaaa  3600
aatagttact atcttcaaag ccacattcgg tcgaaatatc actgattaac aggcggctat  3660
gctggagaag atattgcgca tgacacactc tgacctgtcg cagatattga ttgatggtca  3720
ttccagtctg ctggcgaaat tgctgacgca aaacgcgctc actgcacgat gcctcatcac  3780
aaaatttatc cagcgcaaag ggacttttca ggctagccgc cagccgggta atcagcttat  3840
ccagcaacgt ttcgctggat gttggcggca acgaatcact ggtgtaacga tggcgattca  3900
gcaacatcac caactgcccg aacagcaact cagccatttc gttagcaaac ggcacatgct  3960
gactactttc atgctcaagc tgaccgataa cctgccgcgc ctgcgccatc ccatgctac   4020 ctaagcgcca gtgtggttgc cctgcgctgg cgttaaatcc cggaatcgcc ccctgccagt  4080
caagattcag cttcagacgc tccgggcaat aaataatatt ctgcaaaacc agatcgttaa  4140
cggaagcgta ggagtgttta tcgtcagcat gaatgtaaaa gagatcgcca cgggtaatgc  4200
gataagggcg atcgttgagt acatgcaggc cattaccgcg ccagacaatc accagctcac  4260
aaaaatcatg tgtatgttca gcaaagacat cttgcggata acggtcagcc acagcgactg  4320
cctgctggtc gctggcaaaa aaatcatctt tgagaagttt taactgatgc gccaccgtgg  4380
ctacctcggc cagagaacga agttgattat tcgcaatatg gcgtacaaat acgttgagaa  4440
gattcgcgtt attgcagaaa gccatcccgt ccctggcgaa tatcacgcgg tgaccagtta  4500
aactctcggc gaaaaagcgt cgaaaagtgg ttactgtcgc tgaatccaca gcgataggcg  4560
atgtcagtaa cgctggcctc gctgtggcgt agcagatgtc gggctttcat cagtcgcagg  4620
cggttcaggt atcgctgagg cgtcagtccc gtttgctgct taagctgccg atgtagcgta  4680
cgcagtgaaa gagaaaattg atccgccacg gcatcccaat tcacctcatc ggcaaaatgg  4740
tcctccagcc aggccagaag caagttgaga cgtgatgcgc tgttttccag gttctcctgc  4800
aaactgcttt tacgcagcaa gagcagtaat tgcataaaca agatctcgcg actggcggtc  4860
gagggtaaat catttcccc ttcctgctgt tccatctgtg caaccagctg tcgcacctgc  4920
tgcaatacgc tgtggttaac gcgccagtga acggatact gcccatccag ctcttgtggc  4980
agcaactgat tcagcccggc gagaaactga atcgatccg gcgagcgata cagcacattg  5040
gtcagacaca gattatcggt atgttcatac agatgccgat catgatcgcg tacgaaacag  5100
accgtgccac cggtgatggt atagggctgc ccattaaaca catgaatacc cgtgccatgt  5160
tcgacaatca caatttcatg aaaatcatga tgatgttcag gaaaatccgc ctgcgggagc  5220
cggggttcta tcgccacgga cgcgttacca gacggaaaaa aatccacact atgtaatacg  5280
gtcatactgg cctcctgatg tcgtcaacac ggcgaaatag taatcacgag gtcaggttct  5340
taccttaaat tttcgacgga aaaccacgta aaaaacgtcg atttttcaag atacagcgtg  5400
aattttcagg aaatgcggtg agcatcacat caccacaatt cagcaaattg tgaacatcat  5460
cacgttcatc tttccctggt tgccaatggc ccatttccct gtcagtaacg agaaggtcgc  5520
gaattcaggc gcttttaga ctggtcgtaa tgaaattcag gaggatggtc gacaggagga  5580
cttcttttat gtcaaacttt atacttaaac cgggcgaaaa actaccccaa gacaaactag  5640
aagaattaaa aaaaattaat gatgctgtta aaaaaacgaa aaatttctca aaatacttga  5700
```

-continued

```
ttgacttaag aaaactttt caaattgacg aagtccaagt aacttctgaa tcaaaactct    5760
ttttagctgg tttttagaa ggtgaagctt ctctaaatat tagcactaaa aagctcgcta    5820
cttctaaatt tggtttggtg gttgatcctg aattcaatgt gactcaacat gtcaatgggg   5880
ttaaagtgct ttatttagca ttagaagtat ttaaaacagg gcgtattcgt cataaaagtg    5940
gtagtaatgc aactttagtt ttaactattg acaatcgtca aagtttggaa gaaaaagtaa   6000 ttcctttta tgaacaatat gttgttgcct tcagttctcc agaaaaagtc aaacgtgtag    6060 ctaatttaa agctttgtta gaattattta ataatgacgc tcaccaagat ttagaacaat    6120
tggtaaacaa aatcctacca atttgggatc aaatgcgtaa acaacaagga caaagtaacg   6180
aaggctttcc taatttagaa gcagctcaag actttgctcg taattataaa aaaggtataa   6240
agtaatctag a                                                        6251
```

<210> SEQ ID NO 7
<211> LENGTH: 29
<212> TYPE: DNA
<213> ORGANISM: Artificial Sequence
<220> FEATURE:
<223> OTHER INFORMATION: first strand of double-Stranded I-CeuI DNA
      recognition site

<400> SEQUENCE: 7
cgtaactata acggtcctaa ggtagcgaa                                     29

<210> SEQ ID NO 8
<211> LENGTH: 29
<212> TYPE: DNA
<213> ORGANISM: Artificial Sequence
<220> FEATURE:
<223> OTHER INFORMATION: complementary strand of double-Stranded I-CeuI
      DNA recognition site

<400> SEQUENCE: 8
ttcgctacct taggaccgtt atagttacg                                     29

REGULATED GENETIC SUICIDE MECHANISM COMPOSITIONS AND METHODS

CROSS-REFERENCE TO RELATED APPLICATION

This application claims under 35 U.S.C. §120 as a continuation of U.S. patent application Ser. No. 13/711,482, filed on Dec. 11, 2012, now issued as U.S. Pat. No. 9,045,761, which is a continuation of U.S. patent application Ser. No. 12/490,273, filed on Jun. 23, 2009, now abandoned, which claims the benefit of U.S. Provisional Patent Applications 61/075,687 filed on Jun. 25, 2008 and 61/168,457 filed on Apr. 10, 2009. The contents of each of these related applications are hereby incorporated by reference in their entireties.

REFERENCE TO SEQUENCE LISTING

The present application is being filed along with a Sequence Listing in electronic format. The Sequence Listing is provided as a file entitled SEQUENCELISTING.TXT, created Dec. 11, 2012, which is 28 KB in size. The information in the electronic format of the Sequence Listing is incorporated herein by reference in its entirety.

BACKGROUND OF THE INVENTION

1. Field of the Invention

Embodiments of the present invention relate to compositions and methods for the production, purification, formulation, and use of eubacterial minicells as targeted delivery vehicles for in vivo and in vitro nucleic acid, protein, and small molecule drug delivery as well as a targeted in vivo imaging and diagnostic technology.

2. Description of the Related Art

The following description is provided to aid in understanding the present disclosure, but is not admitted to describe or constitute prior art to the present disclosure. The contents of the articles, patents, and patent applications, and all other documents and electronically available information mentioned or cited in this application, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

Minicells are achromosomal, membrane-encapsulated biological nano-particles (≤400 nm) that are formed by bacteria following a disruption in the normal division apparatus of bacterial cells. In essence, minicells are small, metabolically active replicas of normal bacterial cells with the exception that they contain no chromosomal DNA and as such, are non-dividing and non-viable. Although minicells do not contain chromosomal DNA, plasmid DNA molecules, RNA molecules, native and/or recombinantly expressed proteins, and other metabolites have all been shown to segregate into minicells.

Throughout the last century, minicells have been exploited as tools for research scientists studying cell division, plasmid replication, plasmid segregation, RNA production, protein production, plasmid isolation, plasmid characterization, and plasmid-borne virulence factor production in prokaryotes.

As a result of advances in the fields of microbiology, microbial genetics, and molecular biology, any given minicell, regardless of the parental cell species from which it was derived, can now be engineered and subsequently used as in vivo or in vitro targeted delivery or imaging vehicles.

Minicells are uniquely suited as in vivo delivery and imaging vehicles because they combine many of the singular advantages of other delivery technologies into a single, versatile delivery vehicle. Minicells can be "engineered" to preferentially encapsulate, be coupled to, or absorb biologically active molecules, including various nucleic acids, proteins, and small molecule drugs for subsequent delivery in both therapeutic and prophylactic medicinal applications. As described in much more detail below, minicells have the added advantage in that they can be targeted to specific cell, tissue, and organ types, through the use of several different antibody or affinity-based approaches.

SUMMARY OF THE INVENTION

Some embodiments provide a minicell-producing bacteria comprising: an expressible gene encoding a minicell-producing gene product that modulates one or more of septum formation, binary fission, and chromosome segregation; and an expressible gene encoding an endonuclease, where the chromosome of the minicell-producing bacteria comprises one or more recognition sites of the endonuclease. In some embodiments, the minicell-producing gene is a cell division gene. The cell division gene includes, but is not limited to ftsZ, sulA, ccdB, and sfiC. In some embodiments, the minicell-producing gene is expressed under the control of an inducible promoter. In some embodiments, the endonuclease gene is located on the chromosome of the minicell-producing bacteria. In some embodiments, the endonuclease is a homing endonuclease. The homing endonuclease includes, but is not limited to, I-CeuI, PI-SceI, I-ChuI, I-CpaI, I-SceIII, I-CreI, I-MsoI, I-SceII, I-SceIV, I-CsmI, I-DmoI, I-PorI, PI-TliI, PI-TliII, and PI-ScpI. In some embodiments, the endonuclease is expressed under the control of an inducible promoter. In some embodiments, the minicell-producing bacteria is a Gram-negative bacteria. The Gram-negative bacteria includes, but is not limited to *Campylobacter jejuni, Lactobacillus* spp., *Neisseria gonorrhoeae, Legionella pneumophila, Salmonella* spp., *Shigella* spp., *Pseudomonas aeruginosa*, and *Escherichia coli*. In some embodiments, the minicell-producing bacteria comprising a gene encoding a gene product that is involved in lipopolysaccharide synthesis, where the gene is genetically modified compared to a corresponding wild-type gene. In some embodiments, the gene is a msbB gene that encodes a gene product that causes the bacteria to produce an altered lipid A molecule compared to lipid A molecules in a corresponding wild-type bacteria. In some embodiments, the altered lipid A molecule is deficient with respect to the addition of myristolic acid to the lipid A portion of the lipopolysaccharide molecule compared to lipid A molecules in a corresponding wild-type bacteria. The minicell-producing bacteria can be a Gram-positive bacteria. The Gram-positive bacteria includes, but is not limited to, *Staphylococcus* spp., *Streptococcus* spp., *Bacillus subtilis* or *Bacillus cereus*. In some embodiments, the minicell-producing bacteria comprising a gene that is involved in homologous recombination, where the gene is genetically modified compared to a corresponding wild-type gene, where the minicell-producing bacteria is deficient in DNA damage repair.

Some other embodiments provides a method of making minicells, comprising culturing the minicell-producing bacteria disclosed herein and substantially separating minicells from the minicell-producing parent cells, thereby generating a composition comprising minicells. In some embodiments, the method further comprises inducing minicell formation from the minicell-producing parent cell. In some embodiments, the method further comprises inducing expression of the gene encoding the endonuclease. In some embodiments, minicell formation is induced by the presence of one or more chemical compound selected from isopropyl β-D-1-thiogalactopyranoside (IPTG), rhamnose, arabinose, xylose, fructose, melbiose, and tetracycline. In some embodiments, the expression of the gene encoding the endonuclease is induced by a change in temperature. In some embodiments, the method further comprises purifying the minicells from the composition. In some embodiments, the minicells are substantially separated from the parent cells by a process selected from the group consisting of centrifugation, ultracentrifugation, density gradation, immunoaffinity and immunoprecipitation.

Some other embodiments provide a eubacterial minicell comprising an outer membrane, where the outer membrane comprises Lipid A molecules having no myristolic acid moiety. In some embodiments, the outer membrane of the eubacterial minicell disclosed herein has a composition that results in the reduction of pro-inflammatory immune responses in a mammalian host compared to the outer membrane of eubacterial minicells that are derived from a corresponding wild-type bacteria. In some embodiments, the eubacterial minicell further comprises one or more biologically active compounds. In some embodiments, at least one of the biologically active compounds is selected from the group consisting of a radioisotope, a polypeptide, a nucleic acid, and a small molecule. The biologically active compound can be a small drug molecule, a small molecule imaging agent, a chemotherapeutic agent, or a pro-drug converting enzyme. The biologically active compound can also be a combination of a nucleic acid and a small molecule; a combination of a small molecule imaging agent and a small molecule drug; a combination of a small molecule drug, a small molecule imaging agent, and a nucleic acid; or a combination of a nucleic acid and a polypeptide. In some embodiments, the eubacterial minicell disclosed herein further comprises a cell-surface localized targeting moiety. In some embodiments, the cell-surface localized targeting moiety is a fusion protein, wherein the fusion protein is a fusion of a eubacterial outer membrane anchoring domain and an antibody fragment. In some embodiments, the cell-surface localized targeting moiety is a fusion protein, wherein the fusion protein is a fusion of *Neisserria gonorrheae* IgAP and an antibody fragment that recognizes a mammanlian cell surface antigen. In some embodiments, the mammalian cell surface antigens is selected from the group consisting of adipophilin, AIM-2, BCLX (L), BING-4, CPSF, Cyclin D1, DKK1, ENAH, Ep-CAM, EphA3, FGF5, G250/MN/CAIX, HER-2/neu, IL-13R alpha 2, Intestinal carboxyl esterase, alpha-foetoprotein, M-CSF, MCSP, mdm-2, MMP-2, MUC-1, p53, PBF, PRAME, PSMA, RAGE-1, RGS5, RNF43, RU2AS, secernin 1, SOX10, STEAP1, survivin, Telomerase, WT1, Cdc27, CDK4, CDKN2a, BCR-ABL, BAGE-1, GAGE1-8, GnTV, HERV-K-MEL, KK-LC-1, KM-HN-1, LAGE-1, MAGE-A1, MAGE-A2, MAGE-A3, MAGE-A4, MAGE-A6, MAGE-A9, MAGE-A9, mucin, NA-88, NY-ESO-1, LAGE-2, SAGE, Sp17, SSX-2, SSX-4, TRAG-3, CD-166, and TRP2-INT2.

BRIEF DESCRIPTION OF THE DRAWINGS

FIGS. 4A-D are images showing overexpression of ftsZ and induction of I-CeuI based suicide system causes increased parent cell filamentation.

FIG. 9 shows the single stranded I-CeuI DNA recognition sequence and the double stranded I-CeuI DNA cleavage site.

DETAILED DESCRIPTION

Definitions

Figure 1:
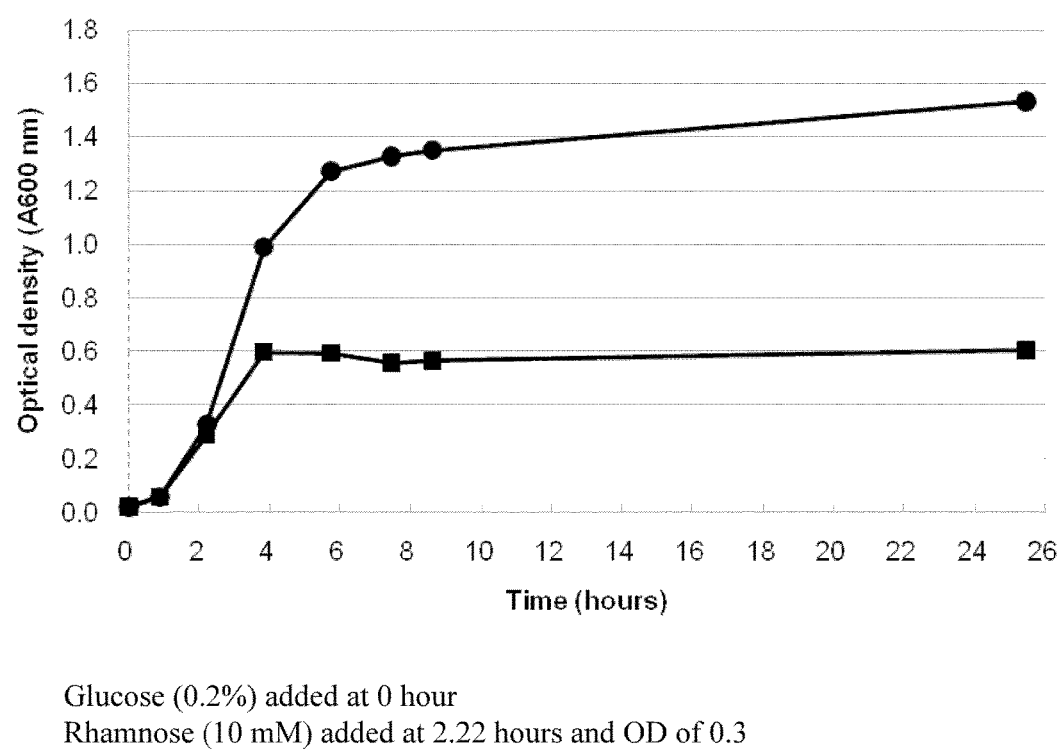
FIG. 1 is a graph showing effects of I-CeuI on *E. coli* culture growth.

The term "cell division gene" used herein refer to a gene that encodes a gene product that participates in the cell division process. Many cell division genes have been discovered and characterized in the art. Examples of cell division genes include, but are not limited to, zipA, sulA, secA, dicA, dicB, dicC, dicF, ftsA, ftsI, ftsN, ftsK, ftsL, ftsQ, ftsW, ftsZ, minC, minD, minE, seqA, ccdB, sfiC, and ddlB.

The term "transgene" used herein refers to a gene or genetic material that has been transferred naturally or by any of a number of genetic engineering techniques from one organism to another. In some embodiments, the transgene is a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In some embodiments, the transgene is an artificially constructed DNA sequence, regardless of whether it contains a gene coding sequence, which is introduced into an organism in which the transgene was previously not found.

As used herein, an agent is said to have been "purified" if its concentration is increased, and/or the concentration of one or more undesirable contaminants is decreased, in a composition relative to the composition from which the agent has been purified. Purification thus encompasses enrichment of an agent in a composition and/or isolation of an agent therefrom.

The term "domain" or "protein domain" used herein refers to a region of a molecule or structure that shares common physical and/or chemical features. Non-limiting examples of protein domains include hydrophobic transmembrane or peripheral membrane binding regions, globular enzymatic or receptor regions, protein-protein interaction domains, and/or nucleic acid binding domains.

The terms "Eubacteria" and "prokaryote" are used herein as these terms are used by those in the art. The term "eubacterial" and "prokaryotic" used herein encompass Eubacteria, including both Gram-negative and Gram-positive bacteria, prokaryotic viruses (e.g., bacteriophage), and obligate intracellular parasites (e.g., Richettsia, Chlamydia, etc.).

The term "nucleic acid" used herein refers to any collection of diverse nucleic acid molecules. A nucleic acid may be a ssDNA, a dsDNA, a ssRNA, a dsRNA, a tRNA (including a rare codon usage tRNA), a mRNA, a ribosomal RNA (rRNA), a peptide nucleic acid (PNA), a DNA:RNA hybrid, an antisense oligonucleotide, a ribozyme, or an aptamer.

The term "overexpression" used herein refers to the expression of a polypeptide or protein encoded by a DNA in a host cell, wherein the polypeptide or protein is either not normally present in the host cell, or wherein the polypeptide or protein is present in the host cell at a higher level than that normally expressed from the endogenous gene encoding the polypeptide or protein.

The term "modulate" as used herein means to interact with a target either directly or indirectly so as to alter the activity of the target to regulate a biological process. The mode of "modulate" includes, but is not limited to, enhancing the activity of the target, inhibiting the activity of the target, limiting the activity of the target, or extending the activity of the target.

Description

Eubacterial minicells are very well suited to serve as targeted delivery and imaging vectors. Because they are derived from bacteria that are often times inherently pathogenic or at least opportunistically pathogenic, it is advantageous that any contaminating parental cells be functionally eliminated from a given population before systemic in vivo administration, particularly if given intravenously. Consequently, the desired minicell formulation would be one in which the residual live parental cell count would be as low as possible as minicells are processed and purified. One way to accomplish this is to introduce a suicide mechanism to kill residual parental cells after the physical separation step has been completed. The enhanced safety profile reduces the risks of infection and sepsis, decrease the possibility of genetic reversions through recombination events with other bacteria and minimize the risks of insertion events in the host. It is preferred that antibiotic resistance markers be eliminated from the bacterial chromosome of the minicell-producing parental cell strain. The elimination of antibiotic resistance gene markers in minicell-producing strains of bacteria is desirable to overcome regulatory hurdles imposed by the U.S. Food and Drug Administration (FDA) for use in humans. The FDA will only tolerate the use of the Kanamycin resistance gene marker for selection purposes for bacteria or bacterial production strains wherein the final product is intended for use in humans. Further, the FDA requires certain standards for the certification of analysis of drug product and the minicell final formulation would have to meet USP and ICH guidelines for purity, absence of aggregates and, absence of particular matter. Thus, upstream, and downstream processing of drug product would have to fall under the company's Chemistry, Manufacturing, and Control (CMC) drug product production activities.

The need for better purification methodologies is a roadblock to the development of minicells derived from pathogenic bacteria. Embodiments of the present invention relate to the incorporation and use of a regulated genetic suicide mechanism that upon exposure to the appropriate signals, introduces irreparable double-stranded breaks to the chromosomes of minicell-producing parental cells resulting in parent cell death. The activation of the suicide mechanism also increases minicell yields compared to other minicell-producing strains, and simultaneously converts all of the minicell-producing parent cells into an irreversible filamentous phenotype. Thus, the suicide mechanism disclosed herein is not limited to promoting death of chromosome-bearing parental bacterial cells but can have other multifunctional actions that act in consort to improve minicell production. In some embodiments, the multifunctional suicide mechanism, the "MSM" system, disclosed herein functions to kill chromosomal-bearing parental cells. In some embodiments, the "MSM" system disclosed herein functions to increase minicell yield. In some embodiments, the "MSM" system disclosed herein functions to induce an irreversible filamentous phenotype exclusively by parental cells to aid in parental cell separation from minicells. In some embodiments, the "MSM" system disclosed herein functions simultaneously to (i) kill chromosomal-bearing parental cells, (ii) increase minicell yield and (iii) induce an irreversible filamentous phenotype exclusively by parental cells to aid in parental cell separation from minicells. The multifunctional actions of the MSM system can improve minicell production and purity using techniques described herein.

Some embodiments relate to compositions and methods for optimizing the yield and purity of minicells produced while reducing or eliminating the number of viable contaminating minicell-producing live eubacterial parent cells by the introduction of a multifunctional genetic suicide mechanism, the "MSM" system, to a minicell-producing parental cell line. Some embodiments also relate to the use of the MSM system for use in synthetic biology applications.

The presence of contaminating live parental cells in a final preparation of minicells is problematic especially for minicells produced from live pathogenic and opportunistically pathogenic bacteria. Safety and CMC issues related to contaminating parental bacterial are of concern when producing biologics or medicaments from bacteria that are intended for use in humans or other mammals because of their ability to cause disease, profound inflammation, and in some cases, death. The compositions and methods of producing bacterial minicells described herein not only improve minicell production and purity but simultaneously improve the safety profile of minicell preparations for in vivo and other uses. Without being limited to the following examples, in vivo applications of high purity and safe minicell preparations can be used in targeted bio-imaging and the therapeutic prevention and treatment of cancer(s), genetic disorders, and infectious diseases. Some embodiments of the present disclosure relates to the incorporation and use of a regulated genetic MSM mechanism that, upon exposure to the appropriate signals, introduces irreparable damage to the chromosomes of minicell-producing parental cells. The suicide mechanism simultaneously facilitates purification techniques designed to better eliminate viable parental cells from preparations of minicells intended for use in a multitude of targeted delivery applications.

The term "regulated genetic suicide mechanism" used herein refer to a mechanism in where a cell or a group of cells is/are stimulated by a known and external source to produce a gene product or products that is/are capable of irreversibly damaging a biologically essential component or cellular process of a cell such that said cell(s) are no longer viable nor able to recover from said event. The term, multifunctional suicide mechanism, MSM, refers to the use of the regulated genetic suicide mechanism to simultaneously induce high level minicell production, parental cell death, and a filamentous phenotype exclusively in the parental cells during induction of the suicide element.

The term "targeted minicell" or "targeted delivery" used herein refers to a minicell composition in which said minicell encapsulates one or more bioactive molecule(s) of choice and displays targeting moieties on the external surfaces of the minicells whether the minicells are (i) fully intact, (ii) protoplasts (outer membrane and cell wall removed) or, (iii) poroplasts (outer membrane removed or permeabilized) such that said moieties specifically bind to, are bound by, or in some other way specifically recognized and thereby deliver, localize to, or aggregate within a specific cell, organ, or tissue type to deliver the molecular contents of said minicell to said target cell, tissue, and organ type in vitro or in vivo. This specific targeting is intended to use minicells to deliver a payload to the targeted cell or tissue.

The in vivo delivery applications using minicells include but are not limited to the targeted delivery of bioactive (synonymous with biologically active) small molecule drugs, bioactive nucleic acids, bioactive proteins, and bioactive lipopolysaccharides to produce a "biological effect" (synonymous with biological response) in an animal. Biological effects include but are not limited to the an effect that kills the target cell (e.g. a cancer cell), replaces a gene that might be deficient or dysfunctional within a particular cell type that is targeted, reduces the expression and/or activity of a protein or signaling molecule that is dysregulated in a particular target cell(s), reduces or increases the secretion of hormone from a particular cell(s), reduces or increases the secretion of proteins from a particular cell(s), stimulates an adaptive cellular immune response to one or more antigens, stimulates an adaptive humoral response against one or more antigens, stimulates both adaptive humoral and cellular immune responses from one or more antigens, stimulates or represses one or more innate immune responses; an effect that positively or negatively impacts a biological process in an animal; and an effect that impacts a biological process in a pathogenic parasite, bacterium, virus, or other pathogenic microbe to treat or prevent a disease in said animal. The biologically active element does not necessarily have to be immunogenic itself in order to induce an immune reaction in the host animal, but can indirectly elicit an immune response as a consequence of its biological activity.

Eubacterial minicells have a distinct advantage in delivery as they can be engineered to target and deliver bioactive molecules to specific cell types in vivo. Targeting can be achieved by coupling to the surface of minicells antibodies or antibody derivatives specific for target cell surface molecules. Alternatively, targeting can be achieved through the genetic engineering of minicell-producing parental strains such that the minicells they produce express and display on the minicell outer membrane antibody fragments or other polypeptides with affinity for target cell specific surface molecules. In this later case, the targeting moiety that is decorated on the minicell surface can be tethered to the membrane by making a chimeric fusion protein between a cell-surface localizing targeting moiety and a transmembrane protein sequence, e.g. IgAP from *Neisserria gonorrhea* (see below). Minicells displaying said antibodies and targeting moieties on their surfaces are used to target specific cell types in vivo to preferentially deliver their bioactive payloads to the targeted tissue, organ, and cell type.

Antibodies, or any portion thereof, intended to aid in the targeting of minicells to a specific tissue, organ, and cell type may be derived from or be part of any immunoglobulin or immunoglobulin subclass, including but not limited to IgA, IgM, IgD, IgG, or IgE. Antibodies of any subclass intended for facilitating the targeting function of minicells may be "humanized", although any antibody of any subclass against a cell specific antigen can be raised in any animal known to generate antibody responses through adaptive immunity to achieve the same goal. In nature, antibodies are generated such that they contain two separate arms with distinct specificities for their respective antigens. Without being limited by the following, a targeting moiety decorating the surface of the minicells could be derived from a phage display library or could be a chimeric fusion protein derived from an extracellular receptor fragment that recognizes a ligand on the target cell.

Antibodies can be engineered to be independently specific for different antigens, such that a single antibody targets two separate antigens simultaneously. This is referred to as a 'bispecific' antibody or 'bispecific' targeting moiety. By way of non-limiting example, antibodies could be engineered to recognize putative surface components of a given eubacterial minicell (e.g., LPS O-antigens) on one Fab' and the other Fab' of the bispecific antibody can be engineered to recognize a cell-specific surface antigen such as those listed below. Additionally, those skilled in the art readily recognize that two separate antibodies, with separate specificities, can be non-covalently attached by coupling them to Protein A/G to form a bispecific antibody derivative capable of adhering to the surface of minicells wherein one antibody within the complex specifically adheres to the surface of said minicell and the other antibody is displayed to specifically recognize and thereby "target" a specific cell, tissue, or organ type in vivo. Similarly, one skilled in the art will recognize that two separate antibodies, with separate specificities, could be covalently link using myriad cross-linking techniques to achieve the same effect.

In some embodiments, minicells are genetically "engineered" to express and display recombinant targeting proteins on their surfaces. This has been successfully accomplished in *Salmonella enterica* by using fusion proteins that contain an Antigen 43-α outer membrane anchoring domain fused to a single chain Fv (scFv) antibody fragment with specificity for Chlam 12 or CTP3. In a similar study, *E. coli* cells expressing and displaying single chain Fv antibody fragments directed towards Coronavirus epitopes fused with the outer membrane localized IgA protease of *Neisseria gonorhoeae* were shown to neutralize Coronavirus and prevent infection in vitro. The same types of strategies could be employed to generate and display targeted fusion proteins on the surfaces of minicells. Other native outer membrane proteins including LamB, OmpF, OmpC, OmpA, OmpD, PhoE, PAL, and various Flagellins have been used as membrane anchoring and display domains in gram negative Enterobacteriacea family members. Generally, the same approach could be used to express and display antibody fragments on the surface of minicells derived from any Enterobacteriaceae or Bacillaceae family member such that said minicells become "specific" targeted delivery vehicles for antigens present on the surface of cell, tissue, or organ types involved in various clinical indications. Achieving this goal is a matter of creating a nucleic acid sequence encoding for a fusion protein between a putative or predicted outer membrane protein or outer membrane localization sequence and an antibody, antibody derivative, or other polypeptide sequence with affinity for a surface molecule present in a given cell, tissue, or organ type.

Another advantage in the use of minicells as delivery vehicles (targeted or non-targeted) is that bioactive molecules may be delivered in combination. For example, it has been demonstrated that minicells can successfully generate humoral immune responses against a heterologous antigen when used as a delivery vehicle for plasmid DNA vaccines. When minicells were used to simultaneously deliver both a DNA vaccine and the corresponding protein, humoral responses were greatly improved upon, illustrating the benefits of the flexibility of minicells with respect to delivery options. In similar fashion, minicells are used to encapsulate and deliver combinations of different nucleic acid types such as plasmid DNA or various antisense interference RNA (e.g., shRNA, siRNA) molecules specific for different mRNA transcripts such that several genes are silenced in a single delivery event. Minicells are also used to deliver two or more small molecule drugs simultaneously such that several intracellular targets are addressed in a single delivery event.

Some embodiments disclosed herein describe a targeted eubacterial mincell capable of delivering several classes of bioactive payload in concert or singularly wherein the final preparation of minicells is substantially free of any remaining viable contaminating parent cells by virtue of the combined effects of an inducible genetic suicide mechanism applied to conventional separation techniques.

1. Minicell Production

Minicells are achromosomal, membrane-encapsulated biological nano-particles (≤400 nm) that are formed by bacteria following a disruption in the normal division apparatus of bacterial cells. In essence, minicells are small, metabolically active replicas of normal bacterial cells with the exception that they contain no chromosomal DNA and as such, are non-dividing and non-viable. Although minicells do not contain chromosomal DNA, the ability of plasmids, RNA, native and/or recombinantly expressed proteins, and other metabolites have all been shown to segregate into minicells. Some methods of construction of minicell-producing bacterial strains are discussed in detail in U.S. patent application Ser. No. 10/154,951, filed May 24, 2002, which is hereby incorporated by reference in its entirety.

Disruptions in the coordination between chromosome replication and cell division lead to minicell formation from the polar region of most rod-shaped prokaryotes. Disruption of the coordination between chromosome replication and cell division can be facilitated through the overexpression of some of the genes involved in septum formation and binary fission. Alternatively, minicells can be produced in strains that harbor mutations in genes that modulate septum formation and binary fission. Impaired chromosome segregation mechanisms can also lead to minicell formation as has been shown in many different prokaryotes.

Similarly, minicell production can be achieved by the overexpression or mutation of genes involved in the segregation of nascent chromosomes into daughter cells. For example, mutations in the parC or mukB loci of *E. coli* have been demonstrated to produce minicells. Both affect separate requisite steps in the chromosome segregation process in Enterobacteriacea. Like the cell division genes described herein, manipulation of wild type levels of any given gene involved in the chromosome segregation process that result in minicell production will have similar effects in other family members.

Because the cell division and chromosome replication processes are so critical to survival, there exists a high level of genetic and functional conservancy amongst prokaryotic family members with respect to genes responsible for these processes. The overexpression or mutation of a cell division gene capable of driving minicell production in one family member, can be used to produce minicells in another. For example, it has been shown that the overexpression *E. coli* FtsZ gene in other Enterobacteriacea family members such as *Salmonella* spp. and *Shigella* spp as well as other class members such as *Pseudomonas* spp. will result in similar levels of minicell production.

The same can be demonstrated in the mutation-based minicell producing strains of the family Enterobacteriacea. For example, deletion of the min locus in any of Enterobacteriacea family members results in minicell production. Cell division genes from the Enterobacteriacea in which mutation can lead to minicell formation include but are not limited to the min genes (MinCDE). While minicell production from the min mutant strains is possible, these strains have limited commercial value in terms of being production strains. The reason for this is that strains with deletions or mutations within the min genes make minicells at constitutively low levels. This presents two problems in terms of commercialization and economies of scale. The first is that minicell yields from these strains are low, which increases production cost. The second is that minicell yields are highly variable with the mutant strains and lot-to-lot variability has enormous impacts on variable production costs associated with manufacturing quality control and regulatory assurances. Using the mutant strains to produce minicells that have encapsulated biologically active molecules such as proteins, RNA, DNA, and other metabolites for delivery made first by the parental cells so that the minicells produced encapsulate said biologically active molecules is problematic. The onset of minicell production in the mutant strains cannot be controlled and occurs at a low level so that the end result is that some minicells will contain no biologically active molecules while others will contain widely variable amounts of biologically active molecules. These shortcomings when taken together or separately greatly restricts the possibility of using these mutant strains to produce minicell at commercially viable yields and/or quality.

Minicell-producing strains that overexpress cell division genes ("overexpressers") are preferred over mutation-based strains because the minicell-production phenotype is controllable when the cell division genes to be overexpressed are placed under the control of an inducible or other conditionally active eubacterial promoter system. Minicell production from strains overexpressing the cell division gene ftsZ was discovered by researchers who were identifying essential cell division genes in *E. coli* using plasmid-based complementation studies. In these studies, the ftsZ gene was present in over 10 copies per cell. The presence of multiple gene copies of ftsZ was demonstrated to produce minicells and extremely long filamented cells. Ultimately, this transition into the irreversible filamentous phenotype negatively impacts minicell yields from strains overexpressing ftsZ from multi-copy plasmids, although the number of minicells produced is still higher than that of any mutant strain. It has since been demonstrated that by reducing the number of ftsZ gene copies to a single, chromosomal duplication, the number of minicells produced increases over those strains where ftsZ is located on multi-copy plasmids and that the filamentous phenotype is less profound. Thus, some preferred composition(s) are inducible minicell-producing strains that overexpress the ftsZ gene from a duplicate, chromosomally integrated copy of ftsZ. The duplicate ftsZ gene used can be derived directly from the species of bacteria in which the minicell-production phenotype is being engineered and can also be derived from the ftsZ gene sequence from other species of bacteria. By way of non-limiting example, overexpression of the ftsZ gene of *Escherichia coli* can be used to generate minicells from *Escherichia coli* and *Salmonella typhimurium*. Resulting strains are comprised of the wild type ftsZ gene and a separate, duplicative, and inducible copy of the ftsZ gene on the chromosome and the inducible genetic suicide mechanism(s) described in greater detail below.

This inducible phenotype approach to minicell production has several distinct advantages over the mutant systems. The first is that because there are no genetic mutations in these strains, there exists no selective pressure during normal growth and the cells of the culture maintain a very stable and normal physiology until the minicell phenotype is induced. The end result is that inducible minicell producing strains are healthier and more stable, which ultimately results in higher yields of minicells as shown in FIG. 3. Another distinct advantage of using the inducible phenotype approach to minicell production is in cases where minicells are to be used to deliver biologically active molecules such as proteins, RNA, DNA, and other metabolites that can be made by the minicell-producing parent cells themselves such that the minicells that are produced encapsulate those biologically active molecules. In these cases, a preferred method is to induce the formation of the biologically active molecule(s) within the parental cells prior to inducing the minicell phenotype so that all of the minicells produced will contain sufficient amounts of the desired molecule(s) to be encapsulated for delivery. These advantages, when used in combination, result in a higher quality and quantity of minicells. By way of non-limiting example, division genes that can be over-expressed to produce minicells in the family Enterobacteriaceae include but are not limited to FtsZ, MinE, SulA, CcdB, and SfiC. A preferred composition is to have a duplicate copy(s) of a cell division gene(s) under the control of an inducible promoter that is stably integrated into the chromosome of a given eubacterial strain. This same strategy could be carried out if the inducible cell division gene cassette were present on a plasmid, cosmid, bacterial artificial chromosome (BAC), recombinant bacteriophage or other episomal DNA molecule present in the cell. Homologs of these gene or gene products from other organisms may also be used.

The novel, inducible MSM system described herein increases minicell yields of the inducible minicell strains even further. The activation of the MSM system results in greater than 10-fold increases in minicell yields compared to other strains that merely over produce ftsZ to promote minicell formation (EXAMPLE 3). It is possible to combine the MSM system with minicell-producing strains that harbor a mutation(s) or deletion(s) in the MinCDE. One preferred embodiment is one in which the MSM system controls both the inducible minicell-producing phenotype, increases minicell yields, results in irreparable cell damage, and promotes a filamentous phenotype amongst the parent cell population. A preferred MSM gene combination is comprised of an inducible minicell-producing strain that over expresses ftsZ or any functional homolog thereof and the inducible expression of a homing endonuclease, preferably the I-CeuI gene from the algae *Chlamydomonas moewusii* as described in more detail below.

The minicell producing and parental cell suicide/filamentation phenotypes that result from activation of the inducible MSM system is not limited to the family Enterobacteriacea but can be reproduced in any rod-shaped bacilli including those from either Gram-negative or Gram-positive origin. For example, minicell producing strains of *Bacillus subtilis* and other members of the Bacillaceae have been studied in great detail. Similar to the minicell producing strains within the family Enterobacteriacea, all of the family Bacillaceae minicell-producing strains are a result of mutations in or overexpression of genes involved in the cell division or chromosome segregation process. Therefore, sufficient evidence exists to support the idea that the manipulation of conserved genes involved in the cell division or chromosome segregation processes of any rod-shaped bacilli family or genera, can be useful in creating minicell producing strains amongst other members of the same family or genera of organism(s). Similarly, and as demonstrated by Table 1 (below), the class of genes useful in creating the MSM system can recognize and destroy the chromosomes of many different rod-shaped gram-negative and gram-positive bacterial species.

Inducible Promoter

Inducible promoter can be used to regulate gene expression by turning on or off gene transcription at certain stages of development of an organism. The activity of these promoters can be induced by the presence or absence of biotic or abiotic factors.

Inducible promoters include, but are not limited to, chemically-regulated promoters and physically-regulated promoters. The transcriptional activity of chemically-regulated promoters including promoters can be regulated by the presence or absence of one or more chemical compounds. The chemical compounds include, but are not limited to, small molecules, nucleic acids, polypeptides, and proteins. Non-limiting examples of the chemical compound are isopropyl β-D-1-thiogalactopyranoside (IPTG), rhamnose, arabinose, xylose, fructose, melbiose, tetracycline, alcohol, steroids, metal, and other compounds. Physically-regulated promoters include promoters whose transcriptional activity regulated by the presence or absence of one or more physical factors, such as water or salt stress, illumination, light or darkness, radiation, low or high temperatures, oxygen, and nitrogen.

2. Separation of Minicells from Parent Cells and Minicell Purification

Because minicells are derived from bacteria that are often times inherently pathogenic or at least opportunistically pathogenic, it is advantageous that any contaminating parental cells be functionally eliminated from a given population before administration. Conventionally, live parental cells have been eliminated through either physical means or biological means.

Physical means include the use of centrifugation-based separation procedures, filtration methodologies, chromatography methodologies, density gradation, immunoaffinity, immunoprecipitation, or any combination thereof. While effective, each has its drawbacks and no one physical separation methodology has been fully adapted to eliminate viable parental cells from minicells. Ultimately for commercial production, filtration methodologies or a combination thereof is the most preferable technique because of its simplicity, practicality, low cost, and scalability. However, current filtration schemes are limited because many contaminating parental cells make it through the filters; and while this can be avoided, there is a compromise in reducing final minicell yield. Ultimately, the design and use of biological factors that influence parent cell size and viability in conjunction with conventional filtration methodologies will result in the best elimination of live cells. As shown below, the MSM system disclosed herein allows for the inducible development of elongated, filamentous parental cells that can be more easily separated from the minicells during production.

Biological elimination is achieved by, but not limited to, the preferential lysis of parental cells, the use of auxotrophic parental strains, treatment with antibiotics, treatment with UV radiation, diaminopimelic acid (DAP) deprivation, selective adsorption of parental cells, and treatment with other DNA damaging agents.

Preferential lysis of parental cells is typically mediated by inducing the lytic cycle of a lysogenic prophage. In the case of minicell producing strains, it is most useful to use a prophage that is lysis competent but defective at re-infection, such that minicells are not subsequently infected and lysed during activation of the lytic phenotype. Alternatively and by way of non-limiting example, individual genes such as those classified as members of the holin gene family, can be expressed to achieve similar levels of lysis without the concerns over re-infection inherent to the use of lysogenic prophages. Both approaches are limited by the fact that the lysis event, regardless of the method used to achieve it, expels unacceptable amounts of free endotoxin into the media. Removal of such large amounts of free endotoxin is time consuming, suffers from lot to lot variability, and is ultimately cost prohibitive.

The use of auxotrophic strains raises concerns over reversion and as such can only be used in cases where minicells are to be produced from commensal or non-pathogenic strains of bacteria. Thus, their application is limited with respect to being used as a method for elimination of live parental cells in minicells production.

Treating minicell preparations with antibiotics raise concerns about the development of antibiotic resistance, especially when making minicells from pathogenic or opportunistically pathogenic parental strains. Regulatory concerns and cost can also be of great concern when using antibiotics to eliminate parental cells from a given minicell production run.

Treatment with UV irradiation can be useful in the elimination of live parental cells on a minicell production run with the exception of the fact that UV irradiation is random and results are highly variable from lot to lot. In addition, this method is not preferred when using minicells to deliver therapeutic or prophylactic nucleic acids as UV irradiation does not discriminate when it randomly damages nucleic acids. For instance, plasmid DNA would also be highly susceptible to DNA damage by UV irradiation and may be rendered ineffective although still effectively delivered by minicells.

DAP deprivation can be useful in the elimination of live parental cells with the exception that this approach is limited by the number of species it can be used for. In other words, not all parent cell species capable of producing minicells require DAP for survival, in which case this approach is of no consequence. Reversion of DAP dependent strains is also a concern with this approach.

Selective adsorption methodologies have yet to be explored with respect to purifying minicells from viable parental cells. Selective adsorption is defined as any process in where parental cells are preferentially adsorbed to a substrate by virtue of their affinity for a substrate. By way of non-limiting example, high affinity protein-protein interactions can be exploited for this use. By way of non-limiting example, the outer membrane protein Invasin from the gram-negative species *Yersinia pseudotuberculosis* has a high affinity for RGD motifs embedded in the protein sequence of Beta-integrins. The gene encoding for invasin under the control an inducible promoter could easily be introduced into a minicell producing strain. Minicells can be produced from this strain prior to the activation of expression of the invasin gene such that the minicells produced do not express or display invasin on their cell surface. Once the desired quantity of minicells is produced from said strain, the viable cells within the culture could be given the signal to produce the invasin protein such that invasin is only expressed and displayed upon viable cells. Once invasin is expressed on the surface of viable parental cells, they can be easily adsorbed to a substrate coated with Beta-integrins or RGD motifs embedded into a synthetic polypeptide or other recombinant protein. Once absorbed, minicells can be selectively purified away from viable parental cells by a number of different means dependent upon the substrate type used. Substrates include but are not limited to solid-phase chromatographic columns used in gravity filtration applications, magnetic beads, ion exchange columns, or HPLC columns. This approach is limited by the disadvantage that no single protein-protein interaction will work for all species of minicell producing parent cells. For instance, the invasin-integrin approach described above would be useful for most Gram-negative Enterobacteriacea family members but not for use with minicell producing Gram-positive Bacillaceae family members.

The use of the previously mentioned filamentous phenotype of minicell-producing parent strains presents a very distinct advantage in terms of aiding in conventional, size-based physical separation technologies such as filtration because it preferentially increases the size of contaminating live cells from a length of ~1 µM to lengths of ~10-15 µM. Minicells however, remain their typical size of ~400 nM. The increased disparity in size between minicells and filamentous parental cells greatly simplifies and obviates filtration schemes as a preferred method of viable parental cell elimination. Filamentation can be induced in rod-shaped eubacteria by several means and the most common include imparting physiological stress upon cells by the addition of high concentrations of salts or by increasing or decreasing the pH of the culture, the overexpression of cell division genes (such as thefts genes as described above), and the induction of the SOS response. The induction of the SOS stress response in bacteria is typically induced by introduction of significant chromosomal damage although other mechanisms have been shown to work. The problem with applying physiological stress to a culture of cells to induce filamentation is that not all cells within the population respond equally to the stress which leads to variations in size that range from parental cells that are not affected at all to those cells that are partially filamented to those that are completely filamented. This unequal response amongst the population limits this approach with respect to reproducibility between purification runs. The same is true for the induction of the SOS response by the addition of an exogenous DNA-damaging agent in that not all of the cells in the population will respond equally to that agent and make filaments.

Given all of the limitations of the biological approaches listed above, a great need remains to develop a universally reliable and effective method of eliminating viable minicell producing parental cells to improve the safety profile of minicells for in vivo applications. To this end, embodiments of the present invention addresses this need and provide methods capable of irreparably damaging the chromosomes of viable minicell producing parental cells by use of a previously undescribed regulated genetic suicide mechanism. The activation of the genetic suicide mechanism simultaneously and irreversibly kills cells while inducing a filamentous phenotype useful for aiding in conventional, filtration-based separation techniques of minicells from live contaminating parental cells.

A preferred and novel way to ensure that all viable parental minicell-producing cells of a population will become uniformly filamentous is to genetically engineer onto the chromosome of minicell-producing strains a gene or set of genes under inducible promoter control that upon activation with inducer will cause filamentation as is achieved with the MSM system described herein (EXAMPLE 4). It was determined that the activation of the genetic suicide (MSM) mechanism described herein causes profound filamentation (EXAMPLE 4). Thus, embodiments of the present invention overcomes the uniformity issues present with other approaches to filamentation by ensuring that any viable cell (a cell with a chromosome) will become filamented on command. It is desirable to circumvent suicide mechanism expression problems associated with inducer uptake and other physiological factors that affect promoter activities to ensure that all cells in a given population will commit suicide when given the appropriate signals. To eliminate insufficient promoter activities and ensure that each cell within the population will become filamented, one preferred promoter system for activating the genetic suicide mechanism is thermoregulated, such as that used by the CI857ts promoter system. Some embodiments comprises a gram-negative or gram positive bacterial strain that contains a nucleic acid further comprising a gene that encodes for a minicell-producing gene (preferably ftsZ) which is operably linked to inducible prokaryotic expression signals, and a second nucleic acid comprising a gene that encodes for a suicide gene that does not lyse the parental cells (preferably the homing endonuclease I-CeuI) which is operably linked to inducible prokaryotic expression signals (preferably CI857ts). The prokaryotic expression signals linked to the minicell producing gene and the suicide gene may be under the control o the same prokaryotic expression signals or different prokaryotic expression signals. Further, the minicell producing gene and the suicide gene may be located on the same or different nucleic acids within a cell, one of which may be an episomal nucleic acid (e.g. plasmid). In some other embodiments, the minicell producing gene and the suicide gene are operably linked in a transcriptional fusion (i.e. on the same mRNA transcript) and under the control of common inducible prokaryotic expression signals. Both the minicell producing gene and the suicide gene may be located in more than one gene copy per cell.

In some embodiments, minicells are substantially separated from the minicell-producing parent cells in a composition comprising minicells. After separation, the compositions comprising the minicells is less than about 99.9%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 65%, 60%, 55%, 50%, 45%, 40%, 35% or 30% free of minicell-producing parent cells.

3. Methods of Inducing Irreparable Chromosomal Damage

The concept that irreparable amounts of damage to the chromosome of a given cell will result in irreversible cell death has been best illustrated by the use of UV irradiation. UV irradiation causes the formation of thymine dimers between adjacent thymine nucleotides in a given DNA molecule. If the number of thymine dimers reaches a threshold level in where insufficient amounts of the proteins involved in the DNA repair of these adducts are available, the cell will effectively die. However, as mentioned above, this approach is severely limited because of its lack of specificity amongst adduct formation sites within the chromosome, its unbiased effects on all nucleic acid types, and variability independent of exposure time.

Irreparable damage to the chromosome can also be achieved by the overexpression of endonucleases. Endonucleases can cleave double stranded DNA at sequence specific cleavage sites. Cleavage can result in blunt-ended or staggered cleavage products dependent upon the restriction enzyme employed.

4. I-CeuI Gene of *Chlamydomonas Moewusii*

The I-CeuI restriction enzyme encoded by the chloroplast DNA (SEQ ID NO:1) of the algae *Chlamydomonas moewusii* is particularly useful for introducing irreparable damage to the chromosome of a broad range of eubacterial minicell producing parental strains. I-CeuI belongs to a unique family of intron encoded Type I restriction enzymes commonly known as homing endonucleases. The I-CeuI homing restriction enzyme specifically cleaves within the 15-19 base pair conserved sequence of the 23S ribosomal RNA (rRNA) rrn operon sites (SEQ ID NO:2). Because 23S rRNA sequences are so conserved amongst eubacteria, I-CeuI may be used to introduce irreparable chromosome damage amongst a wide range of minicell producing parental cell species. The 23S rRNA sites are located at any where from 4-10 distinct positions in most eubacteria (see Table 1), a range of sites that will support irreparable damage. Typically, no 23S rRNA sites are located within the sequence of common plasmid DNA molecules and as such I-CeuI can be used to eliminate parental cells while still allowing for the propagation and segregation of plasmids into minicells with the intent to deliver them as a therapeutic or prophylactic payload. Furthermore, the I-CeuI homing endonuclease operates most efficiently at 42-47° C., thereby making it uniquely suited for use with a thermoregulated promoter system such as the CI857ts promoter system from phage lambda. The CI857ts promoter system is inactivated at temperatures below 39° C. and when shifted to 42-45° C. becomes extraordinarily highly active allowing for the rapid, prolonged, and uniform exposure of each minicell-producing parental cell within the culture to I-CeuI. Activation of this promoter system is largely independent of many prohibitive physiological factors such as inducer uptake.

TABLE 1

List of I-CeuI Recognition Sites Within Different Eubacterial Genomes

| Bacterium | Recognition Sites | ATCC Number |
| --- | --- | --- |
| *Escherichia coli* K12 MG1655 | 7 | ATCC 47076 |
| *Escherichia coli* W3110 | 7 | ATCC 27325 |
| *Escherichia coli* O157:H7 str. Sakai | 7 | ATCC BAA-460 |
| *Shigella dysenteriae* Sd197 | 7 | N/A |
| *Shigella flexneri* 2a str. 2457T | 7 | ATCC 700930 |
| *Shigella boydii* Sb227 | 7 | N/A |
| *Shigella sonnei* Ss046 | 7 | N/A |

TABLE 1-continued

List of I-CeuI Recognition Sites Within Different Eubacterial Genomes

| Bacterium | Recognition Sites | ATCC Number |
|---|---|---|
| Salmonella enterica serovar Typhi Ty2 | 7 | ATCC 700931 |
| Salmonella enterica serovar Typhimurium LT2 | 7 | ATCC 700720 |
| Salmonella enterica subsp. Enterica serovar Choleraesuis str. SC-B67 | 7 | N/A |
| Salmonella enterica subsp. enterica serovar Paratyphi A | 7 | ATCC 9150 |
| Salmonella enterica subsp. Enterica serovar Paratyphi B str. SPB7 | 7 | ATCC BAA-1250 |
| Pseudomonas aeruginosa PA7 | 4 | N/A |
| Pseudomonas aeruginosa PAO1 | 4 | ATCC 15692 |
| Pseudomonas aeruginosa UCBPP-PA14 | 4 | N/A |
| Pseudomonas entomophila str. L48 | 7 | N/A |
| Pseudomonas putida F1 | 6 | ATCC 700007 |
| Pseudomonas stutzeri A1501 | 4 | N/A |
| Vibrio cholerae O395 chromosome 2 | 8 | ATCC 39541 |
| Vibrio cholerae O1 biovar eltor str. N16961 chromosome I | 7 | ATCC 39315 |
| Yersinia pestis Angola | 7 | N/A |
| Neisseria meningitidis MC58 | 4 | ATCC BAA-335 |
| Neisseria meningitidis serogroup C FAM18 | 4 | ATCC 700532 |
| Neisseria gonorrhoeae FA1090 | 4 | ATCC 700825 |
| Listeria monocytogenes strain EGDe | 6 | ATCC BAA-679 |
| Legionella pneumophila subsp. pneumophila str. Philadelphia 1 | 3 | ATCC 33152 |
| Staphylococcus aureus subsp. aureus strain MRSA252 | 5 | N/A |
| Staphylococcus aureus subsp. aureus Mu3 | 5 | ATCC 700698 |
| Staphylococcus epidermidis FDA strain PCI 1200 | 5 | ATCC 12228 |
| Streptococcus pyogenes M1 GAS | 6 | ATCC 700294 |
| Streptococcus pneumoniae R6 | 4 | ATCC BAA-255 |
| Enterococcus faecalis V583 | 4 | ATCC 700802 |
| Clostridium botulinum A str. ATCC 19397 | 8 | ATCC 19397 |
| Clostridium botulinum A str. ATCC 3502 | 9 | ATCC 3502 |
| Clostridium difficile 630 | 11 | ATCC BAA-1382 |

Originally, I-CeuI was isolated from *Chlamydomonas moewusii* to digest purified eubacterial chromosomal DNA molecules for pulse field gel electrophoretic genome analysis. It is commercially available for research use and has been exploited for years by microbiologists studying genome arrangements, genomic rearrangements, performing BAC cloning, and performing other analyses of eubacterial chromosomal DNA. I-CeuI and its Type I family members are unique in that they are not affected by different DNA methylation patterns which can vary greatly amongst the eubacteria. Thus, I-CeuI can be used in a broad range of different minicell producing parent strains. By way of non-limiting example, I-CeuI has been used in vitro to analyze the genomes of *Salmonella*, *Shigella*, *E. coli*, *Pseudomonas* spp., *Aeromonas* spp., *Clostridium* spp., *Staphylococcus* spp., *Bacillus* spp., and *Neisseria* spp. all with equivalent efficiency.

Further, I-CeuI is a member of the subfamily of homing endonucleases known as the LAGLIDADG family. Members of this family number over 100 and all contain the conserved amino acid sequence motif LAGLIDADG that serves as the homodimer interaction interface as well as active site formation and function.

I-CeuI and the other Type I restriction enzymes are not as stringent as the more typical Type II restriction endonucleases with respect to the sequence within which they recognize and perform their respective cleavage reactions. While some bases within the 15-19 base pair sequence are essential for cleavage, others are dispensable. Thus, certain variations of the 15-19 base pair sequence could be engineered such that they differ in sequence at non-critical bases but are still functional cleavage sites. Such sites could be engineered and introduced into the chromosome(s) of minicell producing parent strains as such. These modified cleavage sites would also serve as targets recognized by I-CeuI in vivo or in vitro and could be used to introduce irreparable damage to the chromosome.

5. The Use of Functional Equivalents of I-CeuI

As mentioned previously, the I-CeuI gene of *Chlamydomonas moewusii* is a member of a subclass of homing endonucleases known as the LAGLIDADG family. As such, some embodiments include constructing and utilizing a similar genetic suicide mechanism by utilizing one of the other LAGLIDADG homing endonuclease family members. Members of the LAGLIDADG that can be substituted for I-CeuI include but are not limited to PI-SceI, I-ChuI, I-CpaI, I-SceIII, I-CreI, I-MsoI, I-SceIV, I-CsmI, I-DmoI, I-PorI, PI-TliI, PI-TliII, and PI-ScpI.

Another subfamily of Type I homing endonucleases is termed the GIY-YIG family. Members of this family include but are not limited to the bacteriophage T4 endonuclease I-TevI, Am atpase-6, and SegA.

Yet another subfamily of Type I homing endonucleases is termed the H-N-H family and its members include but are not limited to Eco CoE8, Eco CoE9, Eco CoE2, Eco Mcr, I-HmuI, I-TevIII, Cpc1 gpII, Cpc2 gpII, Avi gpII, Sob gpII, and Sce gpII.

The last subfamily of Type I homing endonucleases is termed the His-Cys box family and its members include but are not limited to I-DirI,I-NaaI, and I-PpoI.

Any or all of the 4 classes of homing endonucleases and their respective DNA target sequences or functional variants thereof can be used to construct a regulated genetic suicide system described herein for use in the elimination of contaminating viable parental cells from minicells.

6. Overexpression of ftsZ in Combination with Activation of the Genetic Suicide Mechanism Generates High Yield Minicell Producing Strains As shown in FIG. 3, the simultaneous activation of I-CeuI and induction of the minicell-producing phenotype worked in concert to have positive effects on minicell production and yield as well as decreased viability and filamentation of contaminating parent cells. EXAMPLE 3 shows high yield minicell-producing strains as the number of minicells produced increased 10-fold when ftsZ and I-CeuI were simultaneously overexpressed. High yield minicell producing strains were defined to be those that generate $10^9$ or greater minicells from a 100 mL starting culture. In addition to generating high yields of minicells, the parental cells became uniformly filamentous upon activation of the I-CeuI and ftsZ genes as shown in FIG. 4. The resulting filamentous phenotype is a factor which is exploited to better facilitate filtration-based minicell purification schemes.

7. Homologous Recombination and Other DNA Damage Repair Pathways

Homologous recombination pathways in eubacteria are highly conserved in terms of function and mechanism of action. Essentially, homologous DNA recombination is mediated by the introduction of a double stranded break in duplex DNA followed by 5' to 3' exonuclease activity that creates single stranded DNA overhangs to be used in an enzyme dependent process known as strand invasion. During strand invasion, homologous regions of two separate duplex DNA molecules base pair with each other. The synthesis of new DNA replaces the region(s) degraded by exonucleases and the result is a short-lived 4-armed heteroduplex DNA structure termed a Holliday junction. The Holliday junction is subject to a helicase dependent process known as branch migration in where the center of the heteroduplex DNA structure can shift from its original position to any other position along the length of any of the 4 arms of the Holliday junction. Once stabilized, the heteroduplex Holliday junction is "resolved" by enzymes termed resolvases and two separate duplex DNA molecules result. In some cases, significant amounts of DNA are transferred from one DNA molecule to the other, hence the term recombination.

It is known that in some instances, double stranded break repair is mediated through the homologous recombination pathway(s) of eubacteria. As stated previously, I-CeuI and the other Type I homing endonuclease family members introduce double stranded breaks and said breaks are subject to repair by homologous recombination. Thus, eliminating the ability of the cell to perform homologous recombination also eliminates the possibility that the double stranded breaks introduced by a Type I homing endonuclease family member will be repaired. Repair of the chromosome is essential to recovery in the case of double stranded breaks and as such, the use of homologous recombination pathway null or conditional mutants in conjunction with said genetic suicide mechanism would be of great benefit in reducing viable contaminating minicell producing parent cells. Some embodiments provide the use of DNA recombination and damage repair pathways to prevent cells containing the genetic suicide mechanism from repairing any chromosomal lesions introduced as a result of the activation of the suicide mechanism.

In the eubacterial family Enterobacteriacea, genes involved in homologous recombination or any step of the process described herein that can be mutated, inactivated, made to be expressed conditionally, or modified in any way as to aid in the elimination of viable contaminating minicell producing parental cells upon the activation of the genetic suicide mechanism include, but are not limited to, recA, recBCD, uvrABC, lexA, recN, recQ, recR, ruv, gyrAB, helD, lig, polA, ssb, recO, mutH, mutL, mutS, topA, uvrD, xseA, srfA, recF, recJ, recE, recT, rusA, dam, dut, xth, or rdgB. Any homologs of said genes can be disrupted in other genera and separate eubacterial families.

Mutations that affect the expression of these genes may be present singularly or in combination with each other. The transcription levels of said gene(s) can be affected by chromosomal deletion, promoter disruption, promoter replacement, promoter modification, or RNA-mediated promoter interference. Translation of said gene(s) can be affected by the expression of antisense mRNA, shRNA, siRNA, or by modification of the Shine Dalgarno sequence. Function of said gene(s) product(s) can be affected by the overexpression of dominant negative version(s) of said gene(s) or other suppressors of said gene(s) such that function is impaired.

Some embodiments provide the replacement of any and all of the genes involved in homologous recombination or double strand break repair pathways listed above with an allele of said gene(s) that is a well characterized temperature sensitive mutant. In an illustrative example of this, the gene product, RecA for example, would function normally at temperatures below 39° C. so to allow for normal growth, physiology, and minicell production but would not function at temperatures higher than 39° C. such that when the temperature of the minicell-producing culture was shifted to 42-45° C. to activate the I-CeuI gene, the RecA molecules present within the cell would be unable to perform their necessary function(s) at a level sufficient enough to aid in the repair of double stranded chromosomal lesions. This approach expedites the effective killing of I-CeuI while providing another level of assurance in the elimination of viable minicell-producing parent cells by providing the cell with no repair mechanism(s).

In some embodiments, the wild type copy of the gene lexA is replaced with a cleavage deficient mutant allele. The LexA protein is a global regulator of the SOS response genes in eubacteria and acts as a repressor to genes within that regulon by juxtaposed occupation of the transcriptional start sites within the promoter regions of SOS response genes. Thus, when the LexA repressor is bound to the promoter regions of the SOS response genes, the genes are inactivated as a result of transcription factor inaccessibility due to LexA-mediated steric hindrance. In the event that cells are subjected to stress such as that provided when double stranded chromosomal DNA breaks are introduced, LexA is cleaved. As a result of cleavage, LexA can no longer bind and repress the activity of SOS response genes. Cleavage can occur through two mechanisms. The first is RecA-mediated cleavage that is stimulated by the activity of RecA proteins in the presence of single stranded DNA. Single stranded DNA is produced by the RecBCD exonuclease complex as the very next sequence of events immediately following the introduction of double stranded chromosomal breaks. The second mechanism is termed "autocleavage" and occurs spontaneously in an intramolecular reaction in response to changes in temperature or pH. Both cleavage mechanisms rely on serine protease activity mediated by the serine residue at amino acid position 119 (S-119) and the lysine residue at amino acid position 156 (L-156). Cleavage occurs between the alanine residue at amino acid position 84 (A-84) and the adjacent glycine residue at amino acid position 85 (G-85). The well characterized cleavage deficient mutant allele of the lexA gene termed lexA3 and its counterpart lexA33 may be used with some embodiments of the present invention.

8. Targeting Minicells

Following production, activation of the genetic suicide mechanism, and subsequent purification, minicells are used as targeted delivery vehicles. Minicells displaying antibodies, antibody derivatives, and other targeting moieties on their surfaces are used to target specific cell types in vivo to preferentially deliver their bioactive payloads to the targeted tissue, organ, and cell type.

Antibodies, or any portion thereof, intended to aid in the targeting of minicells to a specific tissue, organ, and cell type may be derived from or be part of any immunoglobulin subclass, including but not limited to IgA, IgM, IgD, IgG, or IgE. Antibodies of any subclass intended for facilitating the targeting function of minicells may be "humanized", although any antibody of any subclass against a cell specific antigen can be raised in any animal known to generate antibody responses through adaptive immunity to achieve the same goal. In nature, antibodies are generated such that they contain two separate arms with distinct specificities for their respective antigens.

Antibodies can be engineered to be independently specific for different antigens, such that a single antibody targets two separate antigens simultaneously. By way of non-limiting example, antibodies could be engineered to recognize putative surface components of a given eubacterial minicell (e.g., LPS O-antigens) on one arm and the other arm be engineered to recognize a cell-specific surface antigen. In this approach, minicell surface molecules that would be of use include but are not limited to naturally occurring molecules such as lipopolysaccharides (LPS), outer membrane proteins (OMPs), flagellar proteins, pilus proteins, and porins. Alternatively, minicell-producing parental strains can be engineered to express and display protein or LPS molecules on their surfaces that are not naturally occurring or occur in other organisms such that said molecule is recognized by one or more arms of an antibody used to couple targeting antibodies or other targeting moieties to the surfaces of minicells. For example, a protein engineered to express and display the FLAG epitope could be designed and utilized such that one arm or antibody recognizes the FLAG epitope and that the other can recognize a specific cell selective antigen of choice. Additionally, those skilled in the art readily recognize that two separate antibodies, with separate specificities, can be non-covalently attached by coupling them to Protein A/G to form a bi-specific antibody derivative capable of adhering to the surface of minicells wherein one antibody within the complex specifically adheres to the surface of said minicell and the other antibody is displayed to specifically recognize and thereby "target" a specific cell, tissue, or organ type in vivo. Similarly, one skilled in the art will recognize that two separate antibodies, with separate specificities, could be covalently linked using myriad cross-linking techniques to achieve the same effect. All of these potential approaches to targeting are readily recognized by those skilled in the art.

Alternative and preferable to the exogenous addition of antibodies and antibody derivatives, minicells can be "engineered" to express and display recombinant targeting proteins on their surfaces by creating outer membrane fusion proteins that display polypeptide-based targeting moieties. This can be accomplished using any of the outer membrane proteins from Gram-negative bacteria although some outer membrane proteins or regions therein are more suitable for display. This has been successfully accomplished in *Salmonella enterica* by using fusion proteins that contain an Antigen 43-α outer membrane anchoring domain fused to a single chain FcV antibody fragment with specificity for Chlam 12 or CTP3. In a similar study, *E. coli* cells expressing and displaying single chain FcV antibody fragments directed towards Coronavirus epitopes fused with the outer membrane localized, autotransporter IgA protease (IgAP) of *Neisseria gonorrhoeae* were shown to neutralize Coronavirus and prevent infection in vitro. The same types of strategies could be employed to generate and display targeted fusion proteins on the surfaces of minicells. Other native outer membrane proteins including LamB, OmpF, OmpC, OmpA, OmpD, PhoE, PAL, and various Flagellins have been used as membrane anchoring and display domains in gram negative Enterobacteriacea family members. Generally, the same approach could be used to express and display antibody fragments on the surface of minicells derived from any Enterobacteriacea or Bacillaceae family member such that said minicells become "specific" targeted delivery vehicles for antigens present on the surface of cell, tissue, or organ types involved in various clinical indications. One skilled in the art will recognize that achieving this goal is a matter of creating a nucleic acid sequence encoding for a fusion protein between a putative or predicted outer membrane protein or outer membrane localization sequence and an antibody, antibody derivative, or other polypeptide sequence with affinity for a surface molecule present in a given cell, tissue, or organ type.

A preferred embodiment to displaying antibodies, antibody fragments, and any of the other polypeptide-based targeting moieties described herein on the surface of minicells is by fusion with an outer membrane of the "autotransporter" family. The monomeric autotransporters belonging to the sub-class type 5 secretion system of autotransporters (commonly classified as type 5a) are most preferred. Of those autotransporters classified as type 5a, the IgA protease (IgAP) of *Neisseria gonorrhoeae* is preferred. The IgAP autotransporter passenger domain is easily replaced by variable light and heavy antibody chains that are spaced by a short 8-10 repeat proline linker sequence. Sequences from variable heavy (VH) and light (VL) chains are easily identified, isolated, sequenced, and cloned from B-cell hybridomas or any other conventional recombinant DNA or RNA sources of variable light and heavy chain sequence as one ordinarily skilled in the art will readily recognize. Several different antibody fragments and antibody fragment types have been displayed and characterized using the IgAP system in *E. coli* although this approach is entirely novel with respect to their use to target tissues, organs, or cell types in conjunction with use in minicells. Thus, by identifying antibody One skilled in the art will recognize that there are other methods by which targeting of minicells to specific cell, organ, or tissue types could be achieved in addition to the display of antibodies or antibody derivatives that have specificity for cell-specific surface antigens on the surface of minicells. One such method is to express and display on the outer most surface of minicells, non-antibody derived polypeptides that target cell-specific antigens. These polypeptides can be derived but are not limited to, naturally occurring sequences or useful portions thereof and synthetically derived sequences.

Naturally-occurring sequences include those that are known in the art to interact with a cell-specific surface antigen. Examples of these types of interactions include but are not limited to naturally occurring ligand and receptor interactions such as the well-characterized VEGF and the VEGF receptor interaction. For example, VEGF receptors displayed on the surfaces of endothelial or other cells could be targeted by decorating minicells with receptor binding domains of the VEGF protein, thus providing a targetings moiety for delivering minicells to endothelial cells. This would be an alternative to using a scFv fragment of an anti-VEGF receptor as the targeting moiety. In some embodiments, the same naturally occurring surface-localized molecules of the minicell listed above can be engineered using standard molecular biological techniques to create fusion proteins that display the binding portion(s) of these ligands such that said minicells are now capable of specifically recognizing, localizing, and delivering their respective payloads to specific cell types, tissues, and organs of interest.

Synthetic molecules that selectively bind to cell-specific surface antigens, such as mammalian cell surface antigens, may be identified and incorporated into some embodiments of the present invention to serve as targeting moieties. For instance, peptide sequences identified by phage display library can easily be cloned as fusions with any of the native minicell outer membrane proteins as described above to serve as targeting molecules. Similarly, synthetic targeting molecules can be coupled to the surface of minicells using standard chemical conjugation or cross-linking techniques.

Cancer cells, in particular, are highly sought after cell types that can be targeted using minicells. Many cancers display cell surface protein variants or other immunologically distinguishable cell surface markers known collectively as tumor-specific antigens or sometimes referred to as tumor-selective antigens (TSAs). Many antibodies that specifically recognize TSAs, and nucleic acid sequences of the variable regions therefore, are already known in the art. Any of these antibodies can be used in exogenous fashion with invention or alternatively, expressed as a membrane-bound fusion protein and displayed on the surface of the minicell as described above. Many TSAs have been identified to which there no antibodies and therefore nucleic acid sequences of the variable regions of those antibodies currently available. However, methods to produce antibodies to TSAs are well known in the art and the methods disclosed herein are designed such that any and all antibodies to TSAs, or any other cell-specific surface antigen, can be incorporated in to the composition as described.

Tumor-selective antigens include, but are not limited to, adipophilin, AIM-2, BCLX (L), BING-4, CPSF, Cyclin D1, DKK1, ENAH, Ep-CAM, EphA3, FGF5, G250/MN/CAIX, HER-2/neu, IL-13R alpha 2, Intestinal carboxyl esterase, alpha-foetoprotein, M-CSF, MCSP, mdm-2, MMP-2, MUC-1, p53, PBF, PRAME, PSMA, RAGE-1, RGS5, RNF43, RU2AS, secernin 1, SOX10, STEAP1, survivin, Telomerase, WT1, Cdc27, CDK4, CDKN2a, BCR-ABL, BAGE-1, GAGE1-8, GnTV, HERV-K-MEL, KK-LC-1, KM-HN-1, LAGE-1, MAGE A1, MAGE-A2, MAGE-A3, MAGE-A4, MAGE A6, MAGE-A9, MAGE-A9, mucin, NA-88, NY-ESO-1, LAGE-2, SAGE, Sp17, SSX-2, SSX-4, TRAG-3, and TRP2-INT2.

In addition to targeting cancer cells and tumors derived therefrom, embodiments of the present invention also encompass any cell type that displays a selective cell surface antigen(s). For instance, targeting minicells to the pancreas to deliver diabetes drugs, or targeting minicells to dendritic cells or any subclass thereof to deliver protein, carbohydrate, or nucleic acids encoding for antigens for use in vaccine development or innate immune regulation are desirable. A VEGF-based targeting system for endothelial cells is described above. Similarly, targeting minicells to specific cell types of the mucosal epithelium, such as the Peyer's patches of the small intestine, are desirable.

9. Payload Types

Eubacterial minicells are capable of encapsulating and delivering several classes of biologically active compounds that have therapeutic, prophylactic, or diagnostic benefit to an animal. Types of the biologically active compounds (payloads) that can be delivered by minicells include but are not limited to small molecules, nucleic acids, polypeptides, radioisotope, lipids, lipopolysaccharides, and any combination thereof.

The term "small molecule" used herein includes any chemical or other moiety that can act to affect biological processes in a positive or a negative sense. Small molecules can include any number of therapeutic agents presently known and used, or can be small molecules synthesized in a library of such molecules for the purpose of screening for biological function(s). Small molecules are distinguished from macromolecules by size. The small molecules as disclosed herein usually have molecular weight less than about 5,000 daltons (Da), preferably less than about 2,500 Da, more preferably less than 1,000 Da, most preferably less than about 500 Da.

Small molecules include without limitation organic compounds, peptidomimetics and conjugates thereof. As used herein, the term "organic compound" refers to any carbon-based compound other than the macromolecules nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocylcic compounds, imidizoles and phenols. An organic compound as used herein also includes nitrated organic compounds and halogenated (e.g., chlorinated) organic compounds.

"Small molecules" can be synthetic, naturally occurring, and purified from a natural source. Small molecules include, but are not limited to, small molecule drugs and small molecule imaging agents. Types of small molecule drugs include those that prevent, inhibit, stimulate, mimic, or modify a biological or biochemical process within a cell, tissue type, or organ to the benefit of an animal suffering from a disease, whether somatic, germinal, infectious, or otherwise. Examples of drugs include chemotherapeutic agents (cancer drugs), antibiotics, antivirals, antidepressants, antihistamines, anticoagulants, and any other class or subclass thereof as listed in the Physicians Desk Reference.

Small molecules also include the class of molecules collectively known as flourophores. Minicells encapsulating flourophores and displaying cell-specific targeting moieties can be used for in vivo imaging of cell types, tissues, organs, or tumors in an animal. Small molecule flourophores include but are not limited to DAPI, Cybr Gold, Cybr Green, Ethidium Bromide, Alexa Flour, Texas Red, CF SE, and the like. Small molecule chemotherapeutic agents can be targeted and delivered to tissues, cells, and organs using minicells displaying targeting molecules. The term "chemotherapeutic agent" used herein refers to anti-cancer, anti-metastatic, anti-angiogenic, and other anti-hyperproliferative agents. Put simply, a "chemotherapeutic agent" refers to a chemical intended to destroy cells and tissues. Such agents include, but are not limited to: (1) DNA damaging agents and agents that inhibit DNA synthesis such as anthracyclines (doxorubicin, donorubicin, epirubicin), alkylating agents (bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (cisplatin, carboplatin, cis diamminedichloroplatinum), telomerase and topoisomerase inhibitors (Camptosar), (2) tubulin-depolymerizing agents such as taxoids (Paclitaxel, docetaxel, BAY 59-8862), (3) anti-metabolites such as capecitabine, chlorodeoxyadenosine, cytarabine (and its activated form, ara-CMP), cytosine arabinoside, dacabazine, floxuridine, fludarabine, 5-fluorouracil, 5-DFUR, gemcitibine, hydroxyurea, 6-mercaptopurine, methotrexate, pentostatin, trimetrexate, and 6-thioguanine (4) anti-angiogenics (Avastin, thalidomide, sunitinib, lenalidomide), vascular disrupting agents (flavonoids/flavones, DMXAA, combretastatin derivatives such as CA4DP, ZD6126, AVE8062A, etc.), (5) biologics such as antibodies or antibody fragments (Herceptin, Avastin, Panorex, Rituxan, Zevalin, Mylotarg, Campath, Bexar, Erbitux, Lucentis), and (6) endocrine therapy such as aromatase inhibitors (4-hydroandrostendione, exemestane, aminoglutehimide, anastrozole, letozole), anti-estrogens (Tamoxifen, Toremifine, Raoxifene, Faslodex), steroids such as dexamethasone, (7) immuno-modulators: cytokines such as IFN-beta and IL2), inhibitors to integrins, other adhesion proteins and matrix metalloproteinases), (8) histone deacetylase inhibitors, (9) inhibitors of signal transduction such as inhibitors of tyrosine kinases like imatinib (Gleevec), (10) inhibitors of heat shock proteins, (11) retinoids such as all trans retinoic acid, (12) inhibitors of growth factor receptors or the growth factors themselves, (13) anti-mitotic compounds such as navelbine, Paclitaxel, taxotere, vinblastine, vincristine, vindesine, and vinorelbine, (14) anti-inflammatories such as COX inhibitors and (15) cell cycle regulators such as check point regulators and telomerase inhibitors.

Nucleic acids include DNA and RNA and their structural equivalents such as RNA molecules or DNA molecules that utilize phosphothiolate backbones as opposed to the naturally occurring phosphodiester backbones. DNA molecules include episomal DNA (not located on or part of the host cell chromosome) and include plasmid DNA, cosmid DNA, bacteriophage DNA, and bacterial artificial chromosomes (BACs). DNA molecules encode for proteins as described by the central dogma of molecular biology. Thus DNA may encode for proteins of any origin, naturally occurring or synthetic. Likewise, DNA can be engineered to contain "promoter sequences" that are recognized by host cell machinery to activate expression of said encoded proteins. Promoter sequences can be cell specific, tissue specific, or inducer specific. Inducers are exogenously applied signals that help to activate said promoters to produce said proteins. Inducers can be chemical or physical in nature. Many promoter systems are known to those skilled in the art as are the sequences that render them functional. Preferred prokaryotic expression sequences include but are not limited to the pRHA system, the pBAD system, the T7 polymerase system, the pLac system and its myriad derivatives, the pTet system, and the CI857ts system. Preferred eukaryotic promoter systems include but are not limited to the CMV promoter, the SV40 promoter system, and the BGH promoter system. RNAs include but are not limited to messenger RNA (mRNA), transfer RNA (tRNA), and small nuclear RNAs. Many RNAs, classified as antisense RNAs, include but are not limited to small-interfering RNAs (siRNA), short hairpin RNAs (shRNAs), and full length antisense RNAs. Micro RNAs are also included.

Proteins are comprised of polypeptides and are encoded for by DNA. Proteins can be biologically functional, such as enzymes or signaling proteins. Proteins can be structural, such as is the case for actin and the like. Proteins can serve as immunogens or serve other therapeutic purposes (such as supplying or restoring enzyme in a target cell, tissue, organ, or animal). Proteins can aid in the post-endocytosis intracellular transfer of other payload types. For example, proteins such as listeriolysin O from Listeria monocytogenes can be employed to facilitate the transfer of the minicell payload(s) from the endocytotic compartment(s) of a target cell to the cytosol of a target cell. Proteins can also be pro-drug converting enzymes.

Any and all of these payload types may be used in combination or singular at the discretion of the user. One skilled in the art will appreciate and recognize which combinations are to be used for which purposes.

10. Reducing Toxicity of LPS

Safety concerns surrounding the immunogenicity and pyrogenic effects of lipopolysaccharides (LPS), a constitutive component of the minicell outer membrane commonly referred to as endotoxin, is advantageously addressed to further the commercial viability of minicell-based targeted delivery compositions. These safety concerns are advantageously addressed in addition to addressing safety issues that revolve around the possible contamination of minicell-based targeted delivery compositions for use in vivo with viable minicell-producing parent cells. The LPS molecule(s) is essentially comprised of three parts. The first part is the pair of hydrocarbon chains that anchor the molecule into the outer leaflet of the outer membrane which are collectively called the "Lipid A" portion of the molecule. The second is a series of sugar residues commonly referred to the "inner core". The inner core is different from genera to genera but is identical amongst inter-genera members. For example, *Salmonella* and *Shigella* have different inner core structures because they are not members of the same genera while *Salmonella typhi* and *Salmonella typhimurium* share the same inner core structures because they are both members of the genera *Salmonella*. The third component of the LPS molecule, commonly called the "O-antigen" is a series of sugar molecules, the chain length, branch structure, sequence, and composition of varies greatly amongst bacteria, even amongst genera members. Many genes involved in lipopolysaccharide synthesis have been identified and sequenced. For instance, the rfa gene clusters contains many of the genes for LPS core synthesis, includes at least 17 genes.

While the LPS molecule as a whole is very pyrogenic, the major contributor to pyrogenicity with respect to the three components described above is the Lipid A component. The Lipid A component has been shown to bind to and activate Toll-like receptors, a family of signaling molecule present on the surface of mammalian cells that help to recognize specific pathogen associated molecular patterns (PAMP's) of which LPS is a classic member. The potent pyrogenic effects of Lipid A are mediated by a specific portion of the Lipid A molecule that comprising a myristolic acid group attached to one of the hydrocarbon chains. In gram-negative bacteria, this myristolic acid group is added by a single, non-essential gene commonly referred to as msbB. By eliminating the msbB gene, the myristolic acid component is eliminated, and the pyrogenicity of the LPS molecule(s) is drastically reduced. This approach has been exploited to reduce toxicity of LPS in attenuated, living *Salmonella serovars* that happen to colonize hypoxic regions within tumors as an experimental cancer therapy used in human clinical trials. The same msbB gene or its functional equivalent, leads to reduced toxicity of the LPS incorporated into minicells, when deleted from the parental minicell-producing strain(s). The reduced toxicity of the LPS has been shown to result in the reduction of pro-inflammatory immune responses in a mammalian host.

Figure 7:
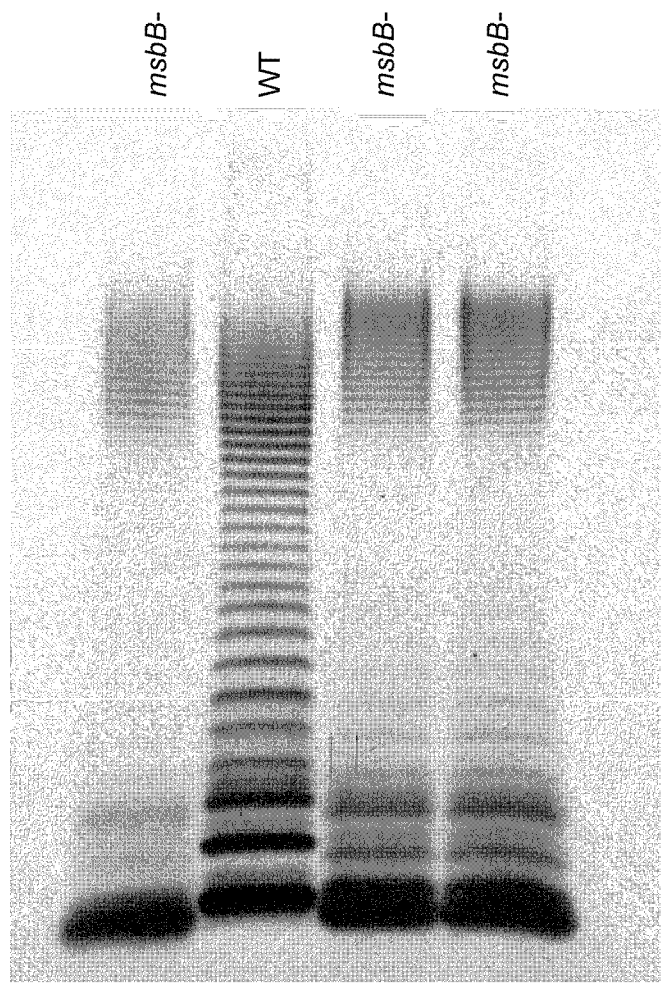
FIG. 7 is a silver stained SDS-PAGE gel showing deletion of the msbb gene in *S. Typhimurium* changes LPS profiles.
Figure 8:
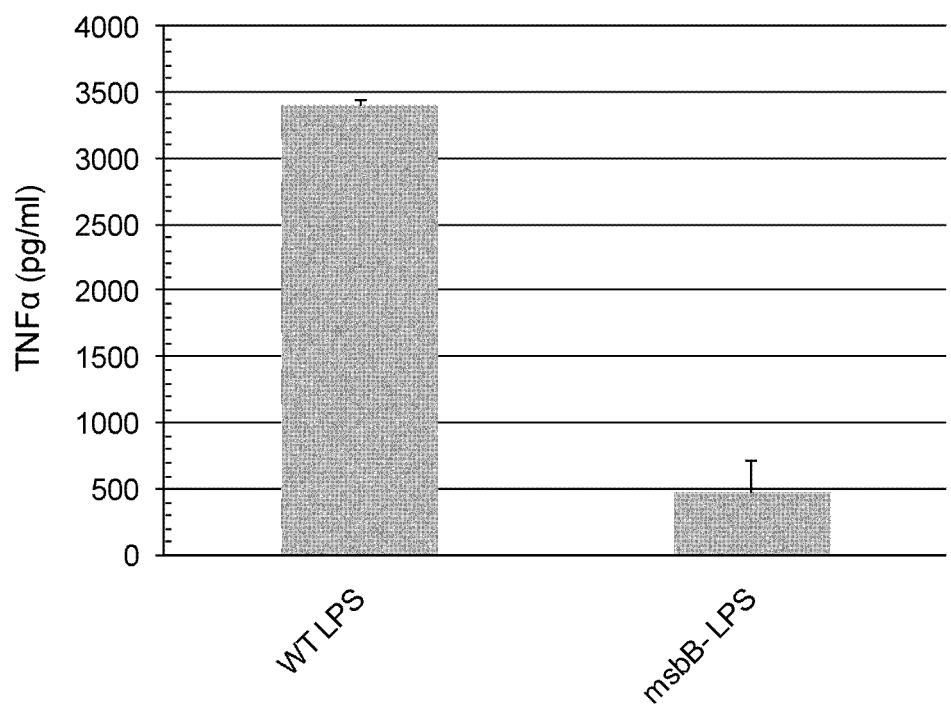
FIG. 8 is a bar graph showing deletion of msbb causes J774.A1 mouse macrophage like cells to produce lower levels of tumor necrosis factor alpha (TNFα) against *S. Typhimurium* LPS.

As shown in FIGS. 7 and 8, successful deletion of msbB in a minicell-producing *Salmonella* strain gave rise to minicells with reduced toxicity as measured by the production of TNF-α by cultured murine macrophages exposed to minicells produced from strains harboring msbB mutations versus those minicells produced from wild type strains.

11. Free Endotoxin Removal

In most in vivo applications, it is desirable to remove any free endotoxin, primarily in the form of free LPS, from the composition. By and large endotoxin removal can be facilitated by the filtration technologies and methodologies employed. As an example, a dead-end filtration step captures minicells and allows smaller molecules such as LPS to pass through the membrane filter, thereby effectively eliminating a large majority of free endotoxin. It is desirable to achieve endotoxin levels for in vivo applications that are at or below the levels mandated by the United States Food and Drug Administration (www.fda.gov). Other conventional and well described approaches that can be used in lieu of or in conjunction with filtration-based endotoxin removal are different chromatographic, immuno-chromatographic, and immuno-precipitation methodologies. In the case of immuno-based methods, a typical method is to use an antibody or other moiety that specifically recognizes and binds to the Lipid A portion of the LPS molecule. The advantage in targeting this segment of the LPS molecule is two-fold. The first advantage is that Lipid A is only exposed when LPS is liberated from the outer membrane of the minicells and thus creates a selective bias towards the removal of only free endotoxin versus the removal of intact minicells. Secondly, many commercially available anti-Lipid A antibodies are available. Coupling antibodies to a solid or semi-solid matrix such as a column or magnetic beads has further advantage in that free endotoxin can be readily and selectively absorbed or adsorbed to the matrix to better facilitate endotoxin removal from minicell compositions. Endotoxin levels in final preparations can be determined by pelleting minicells and analyzing the supernatant for endotoxin levels using the quantitative limulus amoebocyte lysate (LAL) test.

12. Pharmaceutical Compositions.

Another aspect of the present invention relates to compositions, including but not limited to pharmaceutical compositions. The term "composition" used herein refers to a mixture comprising at least one carrier, preferably a physiologically acceptable carrier, and one or more minicell compositions. The term "carrier" used herein refers to a chemical compound that does not inhibit or prevent the incorporation of the biologically active peptide(s) into cells or tissues. A carrier typically is an inert substance that allows an active ingredient to be formulated or compounded into a suitable dosage form (e.g., a pill, a capsule, a gel, a film, a tablet, a microparticle (e.g., a microsphere), a solution; an ointment; a paste, an aerosol, a droplet, a colloid or an emulsion etc.). A "physiologically acceptable carrier" is a carrier suitable for use under physiological conditions that does not abrogate (reduce, inhibit, or prevent) the biological activity and properties of the compound. For example, dimethyl sulfoxide (DMSO) is a carrier as it facilitates the uptake of many organic compounds into the cells or tissues of an organism. Preferably, the carrier is a physiologically acceptable carrier, preferably a pharmaceutically or veterinarily acceptable carrier, in which the minicell composition is disposed.

A "pharmaceutical composition" refers to a composition wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" used herein includes any medium or material that is not biologically or otherwise undesirable, i.e., the carrier may be administered to an organism along with a minicell composition without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated by reference herein into the present application. The terms "therapeutically effective amount" or "pharmaceutically effective amount" mean an amount sufficient to induce or effectuate a measurable response in the target cell, tissue, or body of an organism. What constitutes a therapeutically effective amount will depend on a variety of factors, which the knowledgeable practitioner will take into account in arriving at the desired dosage regimen.

The compositions can further comprise other chemical components, such as diluents and excipients. A "diluent" is a chemical compound diluted in a solvent, preferably an aqueous solvent, that facilitates dissolution of the composition in the solvent, and it may also serve to stabilize the biologically active form of the composition or one or more of its components. Salts dissolved in buffered solutions are utilized as diluents in the art. For example, preferred diluents are buffered solutions containing one or more different salts. A preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the biological activity of a biologically active peptide.

An "excipient" is any more or less inert substance that can be added to a composition in order to confer a suitable property, for example, a suitable consistency or to form a drug. Suitable excipients and carriers include, in particular, fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, methyl cellulose, hydroxypropylmethyl-cellulose, polyacrylate, sodium carboxymethylcellulose, and/or polyvinylpyrrolidone (PVP). If desired, disintegrating agents can also be included, such as cross-linked polyvinyl pyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See WO 98/52547 (which describes microsphere formulations for targeting compounds to the stomach, the formulations comprising an inner core (optionally including a gelled hydrocolloid) containing one or more active ingredients, a membrane comprised of a water insoluble polymer (e.g., ethylcellulose) to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polyvinylpyridine, and polythiodiethylaminomethylethylene.

The compositions can be formulated in any suitable manner. Minicell compositions may be uniformly (homogeneously) or non-uniformly (heterogenously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a composition disclosed herein is compressed into tablet or pill form suitable for oral administration or compounded into a sustained release formulation. When the composition is intended for oral administration but is to be delivered to epithelium in the intestines, it is preferred that the formulation be encapsulated with an enteric coating to protect the formulation and prevent premature release of the minicell compositions included therein. As those in the art will appreciate, the compositions of the invention can be placed into any suitable dosage form. Pills and tablets represent some of such dosage forms. The compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

Some preferred embodiments concern compositions that comprise a bioadhesive, preferably a mucoadhesive, coating. A "bioadhesive coating" is a coating that allows a substance (e.g., a minicell composition) to adhere to a biological surface or substance better than occurs absent the coating. A "mucoadhesive coating" is a preferred bioadhesive coating that allows a substance, for example, a composition to adhere better to mucosa occurs absent the coating. For example, micronized particles (e.g., particles having a mean diameter of about 5, 10, 25, 50, or 100 µm) can be coated with a mucoadhesive. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the composition interacts with the target cell surface transport moiety.

Compositions disclosed herein may be administered to any organism, preferably an animal, preferably a mammal, bird, fish, insect, or arachnid. Preferred mammals include bovine, canine, equine, feline, ovine, and porcine animals, and non-human primates. Humans are particularly preferred. Multiple techniques of administering or delivering a compound exist in the art including, but not limited to, oral, rectal (e.g. an enema or suppository) aerosol (e.g., for nasal or pulmonary delivery), parenteral, and topical administration. Preferably, sufficient quantities of the biologically active peptide are delivered to achieve the intended effect. The particular amount of composition to be delivered will depend on many factors, including the effect to be achieved, the type of organism to which the composition is delivered, delivery route, dosage regimen, and the age, health, and sex of the organism. As such, the particular dosage of a composition incorporated into a given formulation is left to the ordinarily skilled artisan's discretion.

Those skilled in the art will appreciate that when the compositions of the present invention are administered as agents to achieve a particular desired biological result, which may include a therapeutic or protective effect(s) (including vaccination), it may be possible to combine the fusion proteins with a suitable pharmaceutical carrier. The choice of pharmaceutical carrier and the preparation of the fusion protein as a therapeutic or protective agent will depend on the intended use and mode of administration. Suitable formulations and methods of administration of therapeutic agents include those for oral, pulmonary, nasal, buccal, ocular, dermal, rectal, or vaginal delivery.

Depending on the mode of delivery employed, the context-dependent functional entity can be delivered in a variety of pharmaceutically acceptable forms. For example, the context-dependent functional entity can be delivered in the form of a solid, solution, emulsion, dispersion, micelle, liposome, and the like, incorporated into a pill, capsule, tablet, suppository, aerosol, droplet, or spray. Pills, tablets, suppositories, aerosols, powders, droplets, and sprays may have complex, multilayer structures and have a large range of sizes. Aerosols, powders, droplets, and sprays may range from small (1 micron) to large (200 micron) in size.

Pharmaceutical compositions disclosed herein can be used in the form of a solid, a lyophilized powder, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Examples of a stabilizing dry agent includes triulose, preferably at concentrations of 0.1% or greater (See, e.g., U.S. Pat. No. 5,314,695). The active compound is included in the pharmaceutical composition in an amount sufficient to produce the desired effect upon the process or condition of diseases.

13. Production of Other Cell-Based Biologics

Although the disclosure thus far has been to the better purification of minicells with respect to the ratio of minicells to viable parental cells, it is certainly not limited solely to this application. Additionally, the present disclosure can be used in the production of other cell-based biologics as a means of eliminating viable production cells. By way of non-limiting example, the present disclosure can be useful in the production and preparation of enzymes and other proteins, nucleic acids, bacterial ghosts, lipids, biofilms, sugars, and small molecules.

To this end, the present disclosure addresses this need as it provides a method capable of irreparably damaging the chromosomes of viable parental cells by use of a regulated genetic suicide mechanism that has not been previously described.

14. Use of the MSM System in Synthetic Biology

Another aspect of the present invention relates to the use of the MSM system in the field of synthetic biology. As used herein, "synthetic biology" includes the construction and use of a replication competent nucleic acid, a "synthetic genome" or a "synthetic chromosome", wherein said nucleic acid comprises a minimal gene set required for sustained growth in defined media. Synthetic genomes may include one or more genes than are required to constitute a minimal gene set any or all of which may or may not be found together in nature. Synthetic genomes may be created using a transposon-mediated subtractive approach wherein a starting genome has its non-essential genes removed or replaced through a combination of transposon-mediated disruption(s) and homologous recombination(s). Homologous recombination(s) can occur naturally, or may be facilitated by myriad recombination systems including but not limited to the Red recombinase system, the loxP system, the cre recombinase system and the like. Alternatively, the synthetic genome may be created using an additive approach wherein said synthetic genome is rationally designed and constructed de novo. Synthetic genomes constructed using the additive de novo approach may but need not be first constructed in silico. It is desirable to have the synthetic genome further comprising a gene or set of genes that result in a discreet and desired phenotype. For instance, a new organism that can metabolize hydrocarbons to produce biofuels such as hydrogen, ethanol, or bio-diesel(s) could be created and commercialized by the introduction of a synthetic genome containing a gene or set of genes capable of said metabolism in a surrogate microorganism. Other examples include but are not limited to the creation of microorganisms that can fix carbon dioxide directly from the atmosphere, produce industrially relevant by-products or precursors thereto (e.g. sulfite for the production of sulfuric acid), or capable of adding beneficial molecules or removing toxic molecules from the environment.

Once constructed, the synthetic genome may be introduced into a cell derived from a microorganism, including but not limited to a bacterium, using standard transformation techniques, wherein the synthetic genome replaces the original genome of the surrogate microorganism. One method to ensure that the synthetic genome has replaced the original genome is through the incorporation of a selective genetic marker, including but not limited to an antibiotic resistance gene, and selecting for stable transformants. Other selection methodologies known to those skilled in the art will be readily recognized and applicable as alternative selection strategies. Selection strategies can be applied in singular or in plurality. The order of selection is at the sole discretion of the user and can be imparted in any order, temperature, and growth condition.

To ensure the elimination of the original genome from the surrogate microorganism, it is preferred that the chromosome(s) of said surrogate microorganism be destroyed or irreparably damaged at some point during the transformation of the synthetic genome. Preferably, the irreparable destruction of the chromosome(s) would be inducible and would occur prior to the introduction of the synthetic genome into the surrogate microorganism. The MSM system described herein facilitates the inducible and irreparable destruction of the chromosome(s) of bacteria and is easily utilized as a mechanism by which to destroy the original chromosome(s) of the surrogate cell prior to the introduction of the synthetic genome. The modular nature of the MSM system is advantageous because it allows the system to be employed in numerous strains of bacteria including but not limited to those listed in Table 1.

15. The Use of Bacterial Minicells in Synthetic Biology

Another aspect of the present invention relates to use bacterial minicells as the surrogate cell for use in synthetic biology applications as opposed to a bacterium with a chromosome that has been irreparably damaged by the MSM system. Minicells are anucleated cells derived directly from parental bacterial cells. Because bacterial cells are not compartmentalized as compared to eukaryotic cells, all of the DNA synthesis and replication machinery required to replicate a synthetic genome is also present within the minicell. The advantage is that the minicell, by definition, has already "lost" the parental chromosome. Minicells, just as whole cell bacterium, are transformed with synthetic genomes and other nucleic acid types using standard transformation and selection procedures readily recognized by those ordinarily skilled in the art. Selection of transformants can be performed as described above.

Overexpression of DNA synthesis and replication machinery proteins by the minicell-producing parent cell prior to induction of minicell formation will ensure that the synthetic genome is readily synthesized by the minicell upon transformation by providing an abundance of said components by way of segregation into the minicells. Thus, said minicells are enriched with the DNA synthesis and replication machinery prior to transformation. For example, in *E. coli*, genes involved in the replication of the chromosome include but are not limited to dnaA, dnaB, dnaC, ssb, dnaG, polA, dnaE, dnaQ, hole, dnaX, dnaN, dnaX, holA, holB, holC, hold, lig, gyrA, and gyrB. These genes and their functional equivalents can be overexpressed by the minicell-producing parental cell prior to the induction of the minicell phenotype such that they are encapsulated in minicells. Replication and synthesis genes can be overexpressed in any combination and can be present on the chromosome of the parent cell line or on an episomal nucleic acid element such as a plasmid, cosmid, BAC, and the like.

Similarly, genes involved in chromosome partitioning, segregation, and cell division per se may be overexpressed and packaged into the minicell such that said minicells are capable of chromosome partitioning, segregation and cell division as a final requirement in completing the construction of a synthetic organism.

Synthesis of the synthetic genome requires energy in the form of adenosine tri-phosphate (ATPs) molecules and free nucleotides (e.g., adenine, cytosine, guanine, thymine, and uracil or any of their nucleoside or nucleotide derivatives). These molecules passively diffuse across the lipid-bilayers of bacterial minicells and can be added back to supplement transformed minicells until the synthetic genome is stabilized and replicating independently. Polypeptide(s) production from the newly introduced requires free amino acids to incorporate into nascent polypeptide chains. Free amino acids are added back to newly transformed minicells to supplement said minicells with enough free amino acids such as to support nascent protein synthesis from the synthetic genome. Once sufficient levels of metabolic proteins have been synthesized from the synthetic genome by the newly transformed minicells, amino acids may be removed as said minicells are now capable of producing their own stores of amino acids for protein synthesis.

Minicells derived from any prokaryotic source may be used for construction of a synthetic organism using the methods described herein.

16. Minicell Preparations

Some embodiments provide a method of reducing the number of viable eubacterial minicell producing parental cells to improve the safety of minicell preparations intended for in vivo delivery applications with respect to the number of infectious particles administered. Some embodiments comprise a gram-negative or gram positive bacterial strain that contains a nucleic acid encoding for a minicell-producing gene (for example, ftsZ) which is operably linked to inducible prokaryotic expression signals, and a second nucleic acid comprising a gene that encodes for a suicide gene that does not lyse the parental cells (for example, the homing endonuclease I-CeuI) which is operably linked to inducible prokaryotic expression signals (for example, CI857ts). The prokaryotic expression signals linked to the minicell producing gene and the suicide gene may be under the control of the same prokaryotic expression signals or different prokaryotic expression signals. Further, the minicell producing gene and the suicide gene may be located on the same or different nucleic acids within a cell, one of which may be an episomal nucleic acid (e.g. plasmid). Further yet, the minicell producing gene and the suicide gene may be operably linked in a transcriptional fusion (i.e. on the same mRNA transcript) and under the control of common inducible prokaryotic expression signals. Both the minicell producing gene and the suicide gene may be located in more than one gene copy per cell. Eubacterial strains containing the MSM system have the ability to (i) produce high yields of minicells (greater than $10^9$ per 100 mL of culture grown in normal shake flasks, FIG. 3), (ii) introduce irreparable cellular damage that does not lyse cells (FIGS. 1-2, 5-6), and (iii) enter into an irreversible filamentous phenotype (FIG. 4).

Minicells intended for use in in vivo delivery applications are produced from a eubacterial strain that contains said regulated MSM genetic suicide mechanism. Once the desired number of minicells is produced as needed per said application, the genetic suicide mechanism (MSM) would be activated by the exposure to a known stimulus, preferably a shift in temperature, and allowed sufficient time to introduce irreparable damage to the chromosomes of said cells, thereby rendering said cells unviable.

Some embodiments of the present invention relate to induce the minicell production phenotype using the MSM system from an eubacterial minicell-producing strain preferably from, but not limited to, the family Enterobacteriaceae that contains a DNA molecule encoding for a therapeutic or deleterious gene or gene product, such that the resulting minicell contains said DNA molecule by way of encapsulation. Following production of the desired quantity of minicells from a given culture and condition, activation of the genetic suicide mechanism would be stimulated following exposure of said culture or cells to a known signal. The signal would be applied in each step of the purification process to ensure maximal killing of viable cells in the final preparation.

Some embodiments of the present invention relate to induce the minicell production phenotype from an optimized eubacterial minicell-producing strain from, but not limited to, the family Enterobacteriaceae that contains any subclass of RNA, including but not limited to siRNA, antisense RNA, ribozymes, shRNA, and miRNA such that the resulting minicell contains an enriched amount of said RNA molecules by way of encapsulation. Following production of the desired quantity of minicells from said culture and condition, activation of the genetic suicide mechanism (MSM) would be stimulated following exposure of said culture or cells to a known signal. The signal would be applied in each step of the purification process to ensure maximal killing of viable cells in the final preparation.

Some embodiments of the present invention relate to induce the minicell production phenotype from an optimized eubacterial minicell-producing strain from, but not limited to, the family Enterobacteriaceae that contains a protein molecule, such that the resulting minicell contains said protein molecule by way of encapsulation. Following production of the desired quantity of minicells from a given culture and condition, activation of the genetic suicide mechanism would be stimulated following exposure of said culture or cells to a known signal. The signal would be applied in each step of the purification process to ensure maximal killing of viable cells in the final preparation.

Some embodiments of the present invention relate to induce the minicell production phenotype from an optimized eubacterial minicell-producing strain from, but not limited to, the family Enterobacteriaceae that contains a predetermined and deliberate combination of DNA molecules encoding for a therapeutic or deleterious gene or gene product, any subclass of RNA, and/or proteins, such that the resulting minicell contains said combination of molecules by way of encapsulation. Following production of the desired quantity of minicells from a given culture and condition, activation of the genetic suicide mechanism would be stimulated following exposure of said culture or cells to a known signal. The signal would be applied in each step of the purification process to ensure maximal killing of viable cells in the final preparation.

Some embodiments of the present invention relate to induce the minicell production phenotype from an optimized eubacterial minicell-producing strain from, but not limited to, the family Enterobacteriaceae such that it may be "loaded" with small molecules that comprise but are not limited to a drug, a pro-drug, or a hormone following purification. Following production of the desired quantity of "empty" minicells from a given culture and condition, activation of the genetic suicide mechanism would be stimulated following exposure of said culture or cells to a known signal. The signal would be applied in each step of the purification process to ensure maximal killing of viable cells in the final preparation. Following purification, minicells would be "loaded" with said small molecule(s) by incubation in a high concentration of said small molecule at a temperature ranging from 4 to 65° C.

Some embodiments of the present invention relate to induce the minicell production phenotype from an optimized eubacterial minicell-producing strain from, but not limited to, the family Bacillaceae that contains a DNA molecule encoding for a therapeutic or deleterious gene or gene product, such that the resulting minicell contains said DNA molecule by way of encapsulation. Following production of the desired quantity of minicells from a given culture and condition, activation of the genetic suicide mechanism would be stimulated following exposure of said culture or cells to a known signal. The signal would be applied in each step of the purification process to ensure maximal killing of viable cells in the final preparation.

Some embodiments of the present invention relate to induce the minicell production phenotype from an optimized eubacterial minicell-producing strain from, but not limited to, the family Bacillaceae that contains any subclass of RNA, including but not limited to siRNA, antisense RNA, ribozymes, shRNA, and miRNA such that the resulting minicell contains an enriched amount of said RNA molecules by way of encapsulation. Following production of the desired quantity of minicells from said culture and condition, activation of the genetic suicide mechanism would be stimulated following exposure of said culture or cells to a known signal. The signal would be applied in each step of the purification process to ensure maximal killing of viable cells in the final preparation.

Some embodiments of the present invention relate to induce the minicell production phenotype from an optimized eubacterial minicell-producing strain from, but not limited to, the family Bacillaceae that contains a protein molecule, such that the resulting minicell contains said protein molecule by way of encapsulation. Following production of the desired quantity of minicells from a given culture and condition, activation of the genetic suicide mechanism would be stimulated following exposure of said culture or cells to a known signal. The signal would be applied in each step of the purification process to ensure maximal killing of viable cells in the final preparation.

Some embodiments of the present invention relate to induce the minicell production phenotype from an optimized eubacterial minicell-producing strain from, but not limited to, the family Bacillaceae that contains a predetermined and deliberate combination of DNA molecules encoding for a therapeutic or deleterious gene or gene product, any subclass of RNA, and/or proteins, such that the resulting minicell contains said combination of molecules by way of encapsulation. Following production of the desired quantity of minicells from a given culture and condition, activation of the genetic suicide mechanism would be stimulated following exposure of said culture or cells to a known signal. The signal would be applied in each step of the purification process to ensure maximal killing of viable cells in the final preparation.

Some embodiments of the present invention relate to induce the minicell production phenotype from an optimized eubacterial minicell-producing strain from, but not limited to, the family Bacillaceae such that it may be "loaded" with small molecules that comprise but are not limited to a drug, a pro-drug, or a hormone following purification. Following production of the desired quantity of "empty" minicells from a given culture and condition, activation of the genetic suicide mechanism would be stimulated following exposure of said culture or cells to a known signal. The signal would be applied in each step of the purification process to ensure maximal killing of viable cells in the final preparation. Following purification, minicells would be "loaded" with said small molecule(s) by incubation in a high concentration of said small molecule at a predetermined temperature.

In one embodiment, the level of minicell producing parental cell contamination is 1 in $10^7$ minicells.

In another embodiment the level of minicell producing parental cell contamination is 1 in $10^8$ minicells.

In another embodiment the level of minicell producing parental cell contamination is 1 in $10^9$ minicells.

In another embodiment the level of minicell producing parental cell contamination is 1 in $10^{10}$ minicells.

In another embodiment the level of minicell producing parental cell contamination is 1 in $10^{11}$ minicells.

In another embodiment the level of minicell producing parental cell contamination is 1 in $10^{12}$ minicells.

In another embodiment the level of minicell producing parental cell contamination is 1 in $10^{13}$ minicells.

In another embodiment the level of minicell producing parental cell contamination is in $10^{14}$ minicells.

In another embodiment the level of minicell producing parental cell contamination is in $10^{15}$ minicells.

In another embodiment the level of minicell producing parental cell contamination is 1 in $10^{16}$ minicells.

Unless defined otherwise, all technical and scientific terms used herein have the same meaning as commonly understood by one of ordinary skill in the art. Although the present invention has been described with reference to embodiments and examples, it should be understood that various modifications can be made without departing from the spirit of the invention. All references cited herein are expressly incorporated herein by reference in their entirety.

EXAMPLES

Example 1

Effects of I-CeuI on the Growth of *E. Coli*

*E. coli* TOP10 cells were transformed with pVX-55 expression vector (SEQ ID NO:6). The pVX-55 expression vector contains an I-CeuI gene under the control of the rhamnose inducible pRHA promoter system. The transformed *E. coli* cell culture was grown in LB broth supplemented with Kanamycin (50 µg/ml). Glucose (0.2%) was added into the cell culture at 0 hours, and rhamnose (10 mM) were added into the cell culture at 2.22 hours and OD of 0.3. Growth of the bacterium was monitored by measuring absorbance at 600 nm. FIG. 1 shows that the growth of the *E. coli* cell culture was significantly reduced by the induction of I-CeuI homing endonuclease.

Example 2

Effects of I-CeuI on Viability of *E. Coli*

Figure 2:
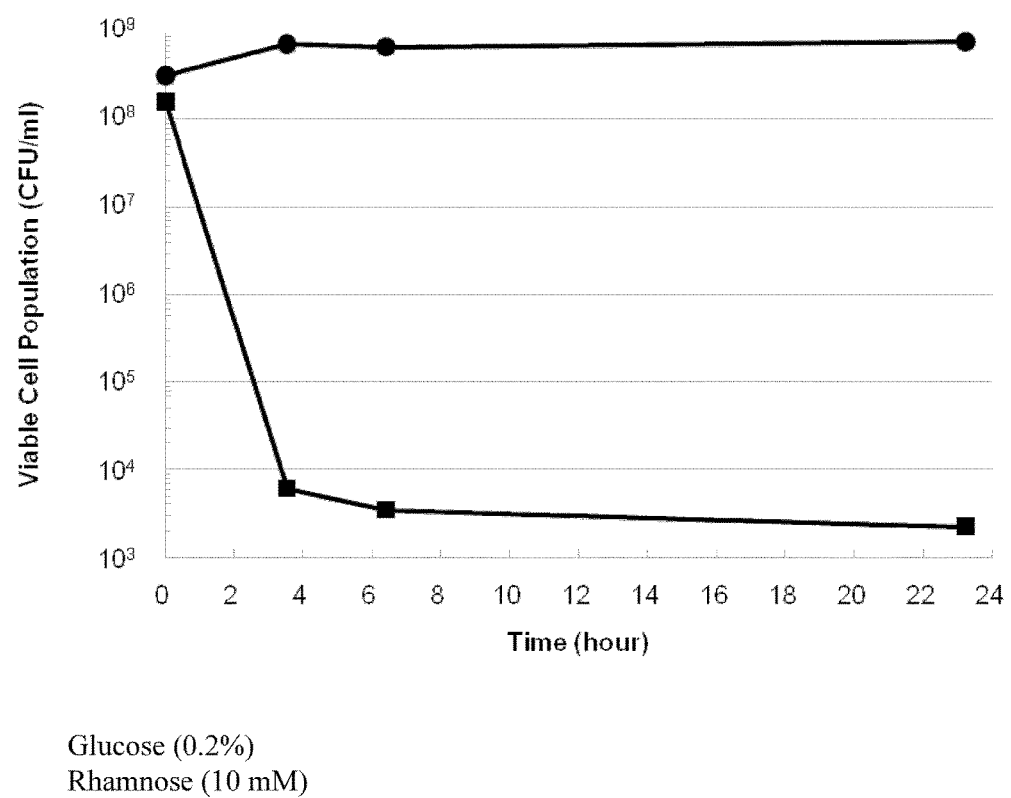
FIG. 2 is a graph showing effects of I-CeuI on *E. coli* viability.

*E. coli* TOP10 cells were transformed with pVX-55 expression vector. The pVX-55 expression vector contains an I-CeuI gene under the control of the rhamnose inducible pRHA promoter system. The *E. coli* cells was cultured in LB broth with Kanamycin (50 µg/ml) supplemented with glucose (0.2%) or rhamnose (10 mM) before spotted on LB agar plates. Viable cell populations (CFU/ml) were determined via colony counts on LB agar plates. No recovery of colonies was observed. FIG. 2 shows that the number of viable *E. coli* cells was significantly reduced by the induction of I-CeuI homing endonuclease.

Example 3

Figure 3A:
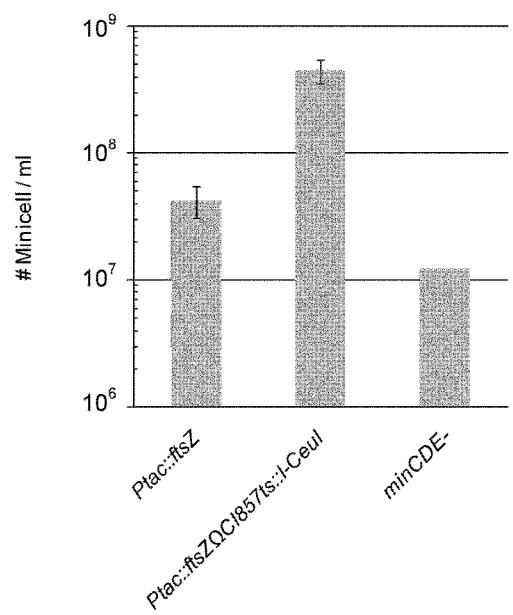
FIGS. 3A and 3B are bar graphs showing simultaneous overexpression of ftsZ and induction of I-CeuI leads to higher minicell yields compared to minCDE-mutants or the overexpression of ftsZ alone.
Figure 3B:
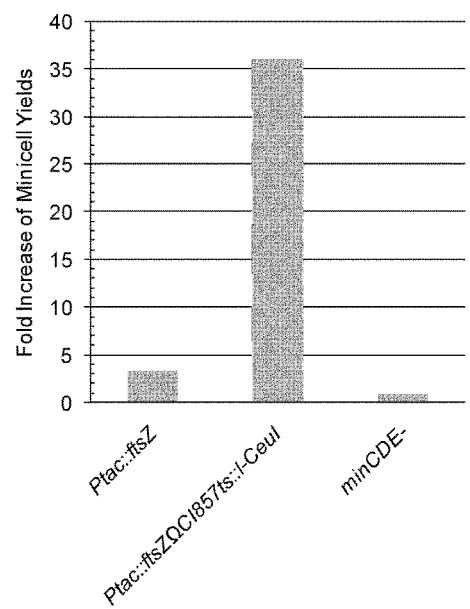

Simultaneous Overexpression of ftsZ and Induction of I-CeuI (MSM) Lead to Higher Minicell Yields An *E. coli* strain containing IPTG inducible ftsZ and minCDE deletion mutation were grown in LB medium. A ftsZ construct (Ptac::ftsZ) and a ftsZ construct with the heat inducible I-CeuI based suicide system (Ptac::ftsZΩCI857ts::I-CeuI) were integrated into the attBk site on the chromosome of the minicell-producing *E. coli* cells, respectively. Minicell productions of the Ptac::ftsZ strain was conducted at 37° C. and minicell products of the Ptac::ftsZΩCI857ts::I-CeuI strain was conducted at 42° C. to induce the I-CeuI based suicide system. Minicells were purified via differential purifications. FIG. 3A shows the numbers of minicells purified from each ml of LB cultures used for minicell productions. FIG. 3B shows the ratios of minicell yields of the IPTG inducible ftsZ strains against the minCDE-strain. FIGS. 3A and 3B demonstrates that when ftsZ and I-CeuI were simultaneously overexpressed in the mini-cell producing cells, the number of minicells produced increased 36-fold compared to the minCDE-strain and increased 10-fold compared to the overexpression of ftsZ alone.

Example 4

Overexpression of ftsZ and Induction of I-CeuI Based Suicide System (MSM) Caused Cell Filamentation

*E. coli* strain VAX8I3 with the inducible ftsZ minicell production system and heat inducible I-CeuI suicide system (pVX-66 (SEQ ID NO:5); Ptac::ftsZΩCI847ts::I-CeuI) were grown in LB medium. At O.D. A600 of 0.1, FtsZ and I-CeuI protein production were induced by elevating temperature to 42° C. After 24 hours of induction, cells were Gram-stained. FIG. 4A shows the *E. coli* strain grown at 30° C. in presence of glucose (0.2%) to suppress I-CeuI and ftsZ overexpression. In FIG. 4B, IPTG (20 µg/ml) was added to overexpress ftsZ, but the expression of I-CeuI was suppressed by incubating at 30° C. In FIG. 4C, the expression of I-CeuI was induced at 42° C., but the overexpression of ftsZ was suppressed by glucose. FIG. 4D shows that simultaneous overexpression of ftsZ and induction of I-CeuI cause more extensive filamentation of cells compared to overexpression of ftsZ in FIG. 4B and induction of I-CeuI expression alone in FIG. 4C. Accordingly, in addition to generating high yields of minicells, simultaneous overexpression of ftsZ and I-CeuI has the advantage of enabling the minicell-producing parent cells to become uniformly filamentous, which can better facilitate filtration-based minicell purification schemes.

Example 5

Induction of I-CeuI Based Suicide System (MSM) Caused Accumulation of Cells with TUNEL Labeled 3'OH DNA Ends Which Indicates Double-Stranded Chromosomal Breaks

Figure 5:
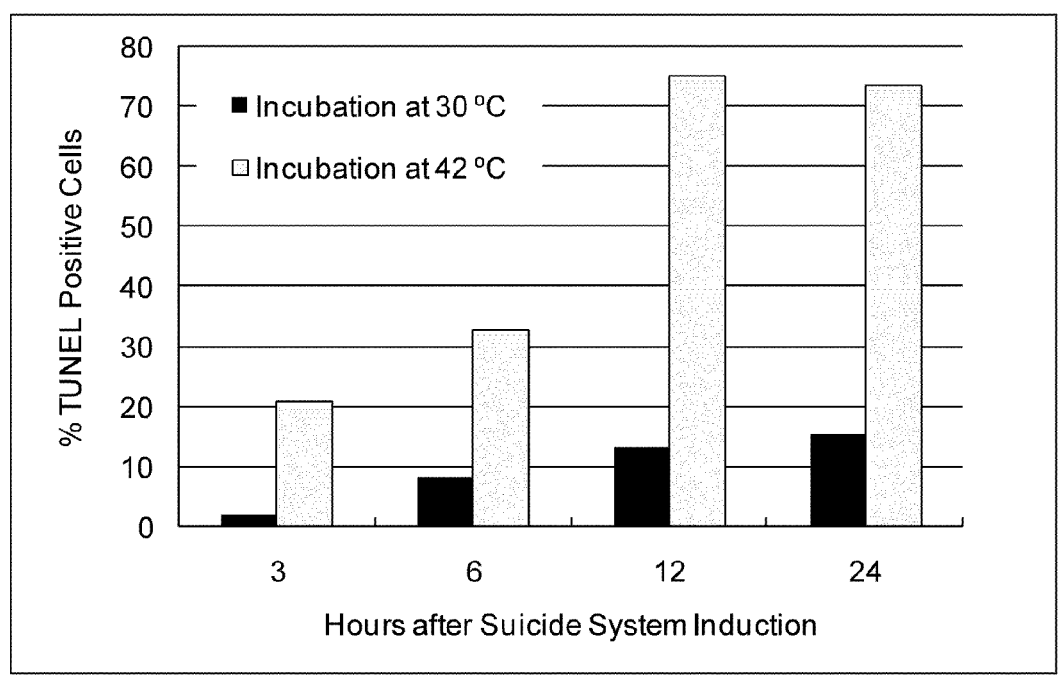
FIG. 5 is a bar graph showing I-CeuI based suicide system introduces irreparable double-stranded chromosomal breaks.

*E. coli* strain VAX8I3, which contains the MSM system under the control of the CI857ts and pTac promoter systems (pVX-66; Ptac::ftsZΩCI857ts::I-CeuI, controlling the expression of I-CeuI and ftsZ, respectively) was grown at either 30° C. or 42° C. in LB medium supplemented with IPTG for 24 hours. Cells were TUNEL (FITC) stained at the indicated time points. As a comparative control, cells were also counter-stained with FM-464 (stains all cells) such that the percentage of TUNEL positive cells amongst the total population were quantified via FACS. FIG. 5 shows that the I-CeuI based suicide system successfully introduced irreparable double-stranded chromosomal breaks in the minicell-producing parent cells, and resulted in the death of over 70% of the cell population within 12 hours after the induction of I-CeuI.

Example 6

Figure 6:
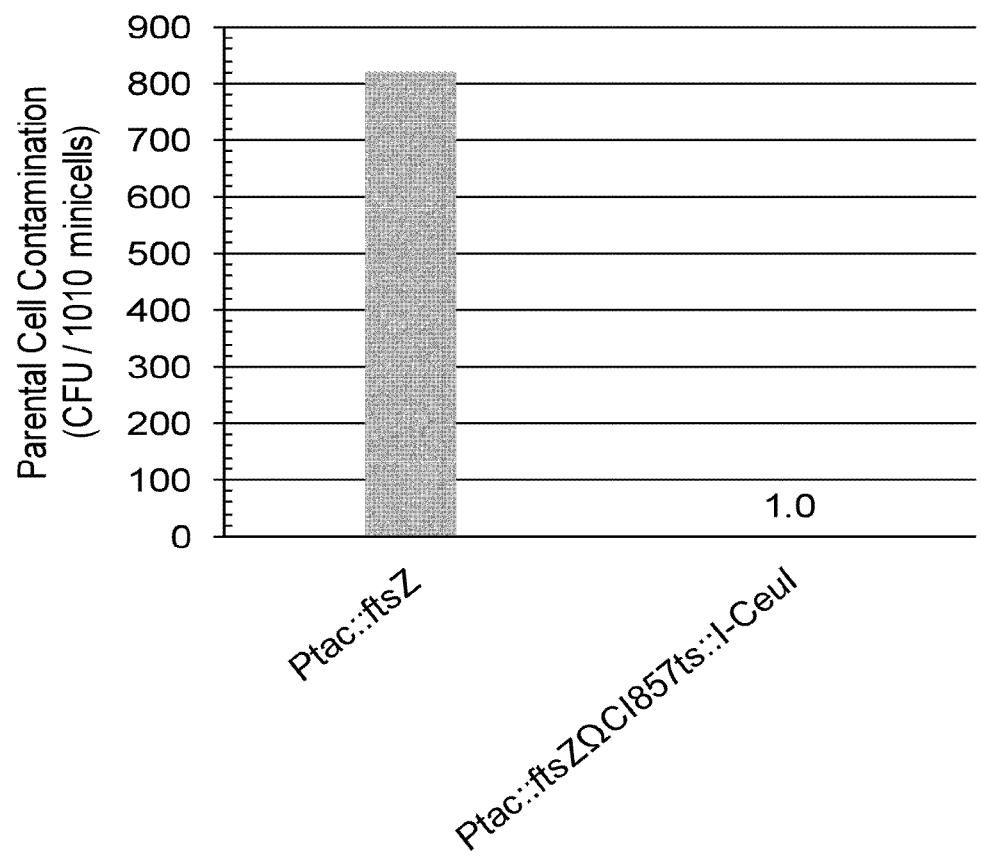
FIG. 6 is a bar graph showing I-CeuI based suicide system reduces parental cell contaminations among purified minicells.

I-CeuI Based Suicide System Reduced Parental Cell Contaminations Among Purified Minicells IPTG inducible ftsZ was integrated into attBk site on *E. coli* chromosome to make a minicell-producing *E. coli* strain (Ptac::ftsZ) via overexpression of ftsZ. Heat-inducible I-CeuI based suicide system was also integrated into the attBk site together with the IPTG inducible ftsZ using the integration plasmid pVX-66 (pVX-66; Ptac::ftsZΩCI857ts::I-CeuI) to make a suicidal minicell-producing *E. coli* strain (Ptac::ftsZΩCI857ts::I-CeuI). The I-CeuI suicide system was activated by incubating at 42° C. Minicells were produced in LB medium supplemented with IPTG and purified via differential purifications. Purified minicells were spread onto LB agar plates supplemented with glucose (0.2%) to examine the presence of live parental *E. coli* cells. After 48 hours of incubation at 30° C., colonies were counted and concentrations of contaminating parental cells were calculated as colony forming unit (CFU) in $10^{10}$ minicells. FIG. 6 shows that the activation of the I-CeuI based suicide system reduced parental cell contamination by over 800 fold.

Example 7

Deletion of msbB in *S. Typhimurium* Changed LPS Profiles

LPS was purified from *S. Typhimurium* strains with wild type msbB (WT) and deleted msbB (msbB-). Deletion of msbB was conducted by substitution of msbB with FRT-cat-FRT via λ Red recombinase system (Red Swap). Acetone dried cells were first treated with DNase I and RNase A followed by Proteinase K treatments. LPS was then extracted via hot water-phenol extraction. LPS was purified via dialysis against water. Purified LPS were separated with SDS-PAGE gel electrophoresis and silver stained. LPS of MsbB mutants have lipid A without myristoyl group. The lack of the myristoyl group reduces molecular weight that can be visualized by shifts in LPS band patterns. FIG. 7 shows that deletion of msbB gene resulted in altered LPS profiles in the *S. Typhimurium* mutant strain as compared to the wild-type *S. Typhimurium* strain.

Example 8

Deletion of msbB Causes J774.A1 Mouse Macrophage Like Cells to Produce Less Amounts of Tumor Necrosis Factor α (TNFα) Against *S. Typhimurium* LPS LPS was purified from *S. Typhimurium* strains with wild type (WT) msbB and *S. Typhimurium* strains harboring msbB deletion mutation, respectively. J774.A1 mouse macrophage-like cells (10⁶ cells) were incubated with 0.1 ng of each type of purified LPS for 12 hours. TNFα concentration was determined via Enzyme Linked Immuno Sorbent Assay (ELISA). FIG. 8 shows that deletion of msbB in a minicell-producing *Salmonella* strain gave rise to minicells with reduced toxicity as measured by the production of TNF-α by cultured murine macrophages.

What is claimed is:

1. A eubacterial minicell derived from a minicell-producing bacteria, wherein the minicell-producing bacteria comprises:
   an expressible cell division gene, wherein the cell division gene is selected from the group consisting of zipA, sulA, secA, dicA, dicB, dicC, dicF, ftsA, ftsI, ftsN, ftsK, ftsL, ftsQ, ftsW, ftsZ, minC, minD, minE, seqA, ccdB, sfiC, and ddlB; and
   an expressible gene encoding a homing endonuclease, wherein the homing endonuclease gene is a transgene, and wherein the chromosome of the minicell-producing bacteria comprises one or more recognition sites of the homing endonuclease.

2. The eubacterial minicell of claim 1, wherein the minicell-producing gene is a transgene.

3. The eubacterial minicell of claim 1, wherein the cell division gene is ftsZ, sulA, ccdB, or sfiC.

4. The eubacterial minicell of claim 1, wherein the cell division gene is expressed under the control of an inducible promoter.

5. The eubacterial minicell of claim 4, wherein the inducible promoter is inducible by the presence of one or more chemical compounds.

6. The eubacterial minicell of claim 1, wherein the homing endonuclease gene is located on the chromosome of the minicell-producing bacteria.

7. The eubacterial minicell of claim 1, wherein the homing endonuclease is selected from the group consisting of I-CeuI, PI-SceI, I-ChuI, I-CpaI, I-SceIII, I-CreI, I-MsoI, I-SceIV, I-CsmI, I-DmoI, I-PorI, PI-TliI, PI-TliII, and PI-ScpI.

8. The eubacterial minicell of claim 1, wherein the homing endonuclease is expressed under the control of an inducible promoter.

9. The minicell-producing bacteria of claim 8, wherein the inducible promoter is a temperature-sensitive promoter.

10. The eubacterial minicell of claim 1, wherein the minicell-producing bacteria is a Gram-negative bacteria.

11. The eubacterial minicell of claim 10, wherein the Gram-negative bacteria is selected from the group consisting of *Campylobacter jejuni*, *Lactobacillus* spp., *Neisseria gonorrhoeae*, *Legionella pneumophila*, *Salmonella* spp., *Shigella* spp., *Pseudomonas aeruginosa*, and *Escherichia coli*.

12. The eubacterial minicell of claim 10, comprising a gene encoding a gene product that is involved in lipopolysaccharide synthesis, wherein the gene is genetically modified compared to a corresponding wild-type gene.

13. The eubacterial minicell of claim 12, wherein the gene is a msbB gene that encodes a gene product that causes the bacteria to produce an altered lipid A molecule compared to lipid A molecules in a corresponding wild-type bacteria.

14. The eubacterial minicell of claim 13, wherein the altered lipid A molecule is deficient with respect to the addition of myristolic acid to the lipid A portion of the lipopolysaccharide molecule compared to lipid A molecules in a corresponding wild-type bacteria.

15. The eubacterial minicell of claim 1, wherein the minicell-producing bacteria is a Gram-positive bacteria.

16. A method of making minicell, comprising:
culturing a minicell-producing bacteria, wherein the minicell-producing bacteria comprises:
an expressible cell division gene, wherein the cell division gene is selected from the group consisting of zipA, sulA, secA, dicA, dicB, dicC, dicF, ftsA, ftsI, tsN, ftsK, ftsL, ftsQ, ftsW, ftsZ, minC, minD, minE, seqA, ccdB, sfiC, and ddlB; and
an expressible gene encoding a homing endonuclease, wherein the homing endonuclease gene is a transgene,
and wherein the chromosome of the minicell-producing bacteria comprises one or more recognition sites of the homing endonuclease; and
substantially separating minicells from the minicell-producing parent cells, thereby generating a composition comprising minicells.

17. The method of claim 16, further comprising inducing expression of the gene encoding the endonuclease.

18. The method of claim 16, further comprising inducing minicell formation from the minicell-producing parent cell.

19. The method of claim 16, further comprising purifying the minicells from the composition.

20. The method of claim 16, wherein the minicells are substantially separated by the parent cells by a process selected from the group consisting of centrifugation, ultracentrifugation, density gradation, immunoaffinity and immunoprecipitation.

21. A eubacterial minicell produced by the method of claim 16.

* * * * *

UNITED STATES PATENT AND TRADEMARK OFFICE
CERTIFICATE OF CORRECTION

PATENT NO. : 9,574,196 B2
APPLICATION NO. : 14/723775
DATED : February 21, 2017
INVENTOR(S) : Matthew J. Giacalone et al.

It is certified that error appears in the above-identified patent and that said Letters Patent is hereby corrected as shown below:

On the Title Page

In Column 1 (page 2, item (56)) at Line 42, Under Other Publications, change "I-CeuI," to --I-CeuI,--.

In Column 1 (page 2, item (56)) at Line 49, Under Other Publications, change "I-CeuI" to --I-CeuI--.

In Column 1 (page 2, item (56)) at Line 58, Under Other Publications, change "I-CeuI" to --I-CeuI--.

In Column 1 (page 2, item (56)) at Line 61, Under Other Publications, change "I-CeuI" to --I-CeuI--.

In Column 1 (page 2, item (56)) at Line 63, Under Other Publications, change "moewusiI" to --moewusii--.

In Column 2 (page 2, item (56)) at Line 13, Under Other Publications, change "I-CeuI" to --I-CeuI--.

In Column 2 (page 2, item (56)) at Line 26, Under Other Publications, change "I-CeuI" to --I-CeuI--.

In Column 2 (page 2, item (56)) at Line 30, Under Other Publications, change "I-CeuI" to --I-CeuI--.

In the Specification

In Column 3 at Line 10 (approx.), Change "melbiose," to --melibiose,--.

In Column 3 at Line 47, Change "Neisserria gonorrheae" to --Neisseria gonorrhoeae--.

In Column 5 at Line 2, Change "Richettsia," to --Rickettsia,--.

In Column 7 at Lines 57-58, Change "Neisserria gonorrhea" to --Neisseria gonorrhoeae--.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,574,196 B2

In Column 8 at Line 43, Change "gonorhoeae" to --gonorrhoeae--.

In Column 9 at Line 16, Change "mincell" to --minicell--.

In Column 12 at Line 28, Change "melbiose," to --melibiose,--.

In Column 14 at Line 35, Change "thefts" to --the fts--.

In Column 16 at Line 34, Change "any where" to --anywhere--.

In Column 18 at Line 64, After "I-MsoI," insert --I-SceII,--.

In Column 22 at Line 65, After "antibody" insert --.--.

In Column 24 at Line 52, Change "heterocylcic" to --heterocyclic--.

In Column 24 at Line 53, Change "imidizoles" to --imidazoles--.

In Column 25 at Line 2, Change "flourophores." to --fluorophores.--.

In Column 25 at Line 3, Change "flourophores" to --fluorophores--.

In Column 25 at Line 5, Change "flourophores" to --fluorophores--.

In Column 25 at Line 7, Change "CF SE," to --CFSE,--.

In Column 25 at Line 17, Change "donorubicin," to --daunorubicin,--.

In Column 25 at Line 20, Change "ifosphamide," to --ifosfamide,--.

In Column 25 at Line 21, Change "mytomycin" to --mitomycin,--.

In Column 25 at Line 29, Change "dacabazine," to --dacarbazine,--.

In Column 25 at Line 30, Change "gemcitibine," to --gemcitabine,--.

In Column 25 at Lines 39-40, Change "aminoglutehimide," to --aminoglutethimide,--.

In Column 25 at Line 40, Change "letozole)," to --letrozole),--.

In Column 25 at Line 41, Change "Toremifine, Raoxifene," to --Toremifene, Raloxifene,--.

In Column 25 at Line 56, Change "phosphothiolate" to --phosphorothioate--.

In Column 29 at Line 35, Change "(heterogenously)" to --(heterogeneously)--.

CERTIFICATE OF CORRECTION (continued)
U.S. Pat. No. 9,574,196 B2

In Column 37 at Line 37, Change "I847" to --I857--.

In Column 38 at Line 18, Change "attBk" to --attBλ--.

In Column 38 at Line 22, Change "attBk" to --attBλ--.

In the Claims

In Column 58 at Line 43, In Claim 7, after "I-MsoI," insert --I-SceII,--.

In Column 59 at Line 11 (approx.), In Claim 16, change "tsN," to --ftsN,--.